US012742173B2

(12) United States Patent
Sharma et al.

(10) Patent No.: US 12,742,173 B2
(45) Date of Patent: Sep. 22, 2026

(54) ANTHOCYANIN BIOSYNTHESIS IN CARROT PLANTS

(71) Applicants: CHR. HANSEN NATURAL COLORS A/S, Hoersholm (DK); AARHUS UNIVERSITY, Aarhus C (DK)

(72) Inventors: Shrikant Sharma, Aarhus (DK); Giuseppe Dionisio, Aarhus (DK); Inger Baeksted Holme, Aarhus (DK); Bjarne Joernsgaard, Hoersholm (DK); Henrik Brinch-Pedersen, Aarhus (DK)

(73) Assignees: Oterra A/S, Hellerup (DK); AARHUS UNIVERSITY, Aarhus (DK)

( * ) Notice: Subject to any disclaimer, the term of this patent is extended or adjusted under 35 U.S.C. 154(b) by 338 days.

(21) Appl. No.: 17/623,644

(22) PCT Filed: Aug. 25, 2020

(86) PCT No.: PCT/EP2020/073732
§ 371 (c)(1),
(2) Date: Dec. 29, 2021

(87) PCT Pub. No.: WO2021/037843
PCT Pub. Date: Mar. 4, 2021

(65) Prior Publication Data

US 2022/0275385 A1 Sep. 1, 2022

(30) Foreign Application Priority Data

Aug. 29, 2019 (EP) .................................... 19194498

(51) Int. Cl.
*A01H 5/06* (2018.01)
*C07K 14/415* (2006.01)
*C12N 15/82* (2006.01)

(52) U.S. Cl.
CPC ........... *C12N 15/8216* (2013.01); *A01H 5/06* (2013.01); *C07K 14/415* (2013.01)

(58) Field of Classification Search
None
See application file for complete search history.

(56) References Cited

U.S. PATENT DOCUMENTS 10,106,806 B2 10/2018 Sundstrom

FOREIGN PATENT DOCUMENTS

WO 2018/055108 A1 3/2018

OTHER PUBLICATIONS

Xu et al., A MYB transcription factor, DcMYB6, is involved in regulating anthocyanin biosynthesis in purple carrot taproots, 2017, Scientific Reports vol. 7, Article No. 45324, pp. 1-9 (Year: 2017).*

Xu et al., Changing Carrot Color: Insertions in DcMYB7 Alter the Regulation of Anthocyanin Biosynthesis and Modification, Jun. 2019, Plant Physiology, vol. 181(1), pp. 195-207 (Year: 2019).*

Massimo Iorizzo et al: "A Cluster of MYB Transcription Factors Regulates Anthocyanin Biosynthesis in Carrot (*Daucus carota* L.) Root and Petiole", Frontiers in Plant Science, vol. 9, Jan. 14, 2019 (Jan. 14, 2019), XP55659471, DOI: 10.3389/fpls.2018.01927 the whole document.

Naing Aung Htay et al: "Roles of R2R3-MYB transcription factors in transcriptional regulation of anthocyanin biosynthesis in horticultural plants", Plant Molecular Biology, Springer, Dordrecht, NL, vol. 98, No. 1, Aug. 30, 2018 (Aug. 30, 2018), pp. 1-18, XP036596920, ISSN: 0167-4412, DOI: 10.1007/S11103-018-0771-4 [retrieved on Aug. 30, 2018] the whole document.

Yildiz Mehtap et al: "Expression and mapping of anthocyanin biosynthesis genes in carrot", Theoretical and applied genetics; International Journal of Plant Breeding Research, Springer, Berlin, DE, vol. 126, No. 7, Mar. 24, 2013 (Mar. 24, 2013), pp. 1689-1702, XP035333158, ISSN: 0040-5752, DOI: 10.1007/S00122-013-2084-Y [retrieved on Mar. 24, 2013] the whole document.

Elyana Cuevas Montilla et al: "Anthocyanin Composition of Black Carrot (*Daucus carota* ssp. sativus var. atrorubens Alef.) Cultivars Antonia, Beta Sweet, Deep Purple, and Purple Haze", Journal of Agricultural and Food Chemistry, vol. 59, No. 7, Mar. 7, 2011 (Mar. 7, 2011), pp. 3385-3390, XP5553326, ISSN: 0021-8561, DOI: 10.1021/jf104724k the whole document.

Yi-Yun Chen et al: "Identification and Characterization of DcUSAGTI, a UDP-Glucose: Sinapic Acid Glucosyltransferase from Purple Carrot Taproots", PLOS One, vol. 11, No. 5, May 12, 2016 (May 12, 2016), p. e0154938, XP55659646, DOI: 10.1371/journal.pone.0154938 the whole document.

Anonymous: "*Daucus carota* subp. sativus cultivar DH1 chromosome 5, ASM162521v1, w—Nucleotide—NCBI", Jun. 27, 2016 (Jun. 27, 2016), XP55660203, Retrieved from the Internet: URL:https://www.ncbi.nlm.nih.gov/nuccore/NC_030385.1?from=3523860&to=3526166&report=genbank&strand=true [retrieved on Jan. 21, 2020] cited in the application the whole document.

ISR for PCT/EP2020/07372.

(Continued)

*Primary Examiner* — Amjad Abraham
*Assistant Examiner* — Christina L Meadows
(74) *Attorney, Agent, or Firm* — Jerold I Schneider; SCHNEIDER IP LAW

(57) ABSTRACT

The present invention provides transgenic carrot plants comprising at least one heterologous DNA sequence encoding: (a) a promoter of a transcription factor gene; or (b) a transcription factor geneoperably linked to a promoter; wherein the heterologous DNA sequence increases the expression of at least one gene encoding a sinapic acid glucosyltransferase (USAGT). The transcription factor gene is preferably DcMYB90 (SEQ ID NO:1) or DcEGL1 (SEQ ID NO:2) or a sequence having at least 80% identity to the sequence of SEQ ID NO:1 or at least 80% identity to the sequence of SEQ ID NO:2, wherein the sequence encodes a transcription factor protein increasing the expression of sinapic acid glucosyltransferase (USAGT) having the sequence of SEQ ID NO:4.

7 Claims, 16 Drawing Sheets

Specification includes a Sequence Listing.

(56) References Cited

OTHER PUBLICATIONS

Third Party Observation for Applicant' Corresponding European Application citing Holme and Sharma.
Third Party Observation for Applicant' Corresponding European Application citing Holme, Xu, Sharma, Xu, and U.S. Pat. No. 10,106,806.
Third Party Observation for Applicant' Corresponding European Application citing Holme.
Sharma 2018, PhD Dissertation, Anthocyanin Biosynthesis in Carrot, Aarhus University.
Xu, DcMYB113, a root-specific R2R3-MYB, conditions anthocyanin biosynthesis . . . Plant Biotechnology Journal 2020, vol. 18, pp. 1585-1597.
Holme, Inger Baeksted, A Roadmap to Modulated Anthocyanin Compositions in Carrots, Plants, 2021, vol. 10.
Xiong, DcMYB7 regulates anthocyanin modification, Plant Physiology Preview, Jun. 18, 2019.
Sharma, Cyanidin based anthocyanin in orange carrot . . . Plant Molecular Biology, published online Apr. 8, 2020.

* cited by examiner

| Gene Name | Gene ID | Accession No. | Primer Sequence (5' > 3') | | SEQ ID NO |
|---|---|---|---|---|---|
| DcMYB90 | 108221186 | XM_017395082 | Fw | ATGAGCTATTCCAAGGGCATGAA | 8 |
| | | | Rv | ATGGCAGAGATCCTGAGAAAGC | 9 |
| DcMYB75a-like | 108213641 | XM_017385443 | Fw | ATGCATTCAAAGGGTATGAAGATTAC | 10 |
| | | | Rv | TCAACTATAGTCCTGGTTCAGAAGATC | 11 |
| DcMYB75b-like | 108212502 | XM_017384225 | Fw | ATGAAGAATTGTAATCCTTTGAAGGTG | 12 |
| | | | Rv | TTAAATGTAATCTAAGTTGAGAAGATTCCAAA | 13 |
| DcEGL1 | 108210744 | XM_017382138 | Fw | TTATAACCGACTCAATCGGACATG | 14 |
| | | | Rv | TTAGGACTTTCTGGTAACTCGTTGA | 15 |
| Dc_bHLH-A | 108204485 | XM_017373947 | Fw | ATGGCTTCACCACCACCTTA | 16 |
| | | | Rv | CTCCATCTGAATTAACCTAGTAACTCA | 17 |

Fig. 1

| Entry Vector | Component | Source plasmid | Primer | Sequence (5' > 3') | SEQ ID NO |
|---|---|---|---|---|---|
| pE-M90_M1 | ZeoR | pGAPZ/pPICZ[2] | Fw | GAATTCTGATCTGAGACCCGGACGTGGGCAGGTGGTGTTGACAATTAATC | 18 |
| | | | Rv | ATTTTGCCGTCAAGGCGATATCGACAAAGGAAAAGGG | 19 |
| | HiCopyOri | pTC241 | Fw | CTTTTCCTTTGTCGATATCAAATCCCTTAACGTG | 20 |
| | | | Rv | GATCTCGAGGATCATGAGCAGGTGCGCAGGAAAGAACATGTGAGCAAA | 21 |
| | CaMV 35S (P) | pCambia130035Su[3] | Fw | CACCTGCTCATGATCCTCGAGATCCGTCAACAT | 22 |
| | | | Rv | GGTGCCTGAGACCGGTCGTCCTCTCCAAATGAAA | 23 |
| | *DcMYB90* | pTOPO_M90_A | Fw | GACCGGTCTCAGGCACCATGAGCTATTCCAAGGGCATGAA | 24 |
| | | | Rv | GCTTGGTCTCAGTCGTTATAACCGACTCAATCGGACATG | 25 |
| | NOS (T) | pVec8-GFP[4] | Fw | ACGATCGGGGAAATTCAAGCTTGGTCTCAGTCG | 26 |
| | | | Rv | CACCTGCCCACGTCCGGAATTCGTCACCGGGCGATCTAG | 27 |
| pE-E1_M2 | Mod2 backbone[1] | pEntryM1_M90 | Fw | GAATTCCCCGGTGACGCAGGTGGTGTTGACAATTAATC | 28 |
| | | | Rv | CTCGAGGGTCCCCTGGCAGGTGCGCAGGAAAGAACATGTGAGCAAA | 29 |
| | CaMV 35S (P) | pCambia130035Su[3] | Fw | CACCTGCCAGGGGACCCTCGAGATCCGTCAACAT | 30 |
| | | | Rv | GGTCCAATGAGACCTCTAGAGGTCGTCCTCTCCAAATGAAA | 31 |
| | *DcEGL1* | pTOPO_E1_A | Fw | ACCTCTAGAGGTCTCATTGGACCATGGCAGAGATCCTGAGAAAGC | 32 |
| | | | Rv | ATTCGGTCTCACCATAGTCGACTTAGGACTTTCTGGTAACTCGTTGA | 33 |
| | NOS (T) | pVec8-GFP[4] | Fw | GTCGACTATGGTGAGACCGAATTTCCCCGATCGT | 34 |
| | | | Rv | CACCTGCGTCACCGGGGAATTCCGATCTAGTAACATAGATG | 35 |
| pD_M1-M2 | Plac (P) | pCR4 Blunt[2] | Fw | TAATACGACTCACTATATCCGGATCAAAAGCAGGTGATGTTCTTTCCTGCGTTATCCCCTGATTCTGTGG | 36 |
| | | | Rv | CTCCTCGCCCTTGCTCACCATGGTATAAGCTGTTTCCTGTGTGAAATTG | 37 |
| | BFP | pBad-EBFP2[5] | Fw | GGAAACAGCTTATACCATGGTGAGCAAGGGCGAGGAG | 38 |
| | | | Rv | GGAACAAAAGCTGGAGCTCCGGTGACGCAGGTGTTACTTGTACAGCTCGTCCATGC | 39 |

Fig. 2

| Primer Pair Code | Gene code | Gene Name | Gene ID | Accession ID | Primer Sequence (5' > 3') | | SEQ ID NO | Amplicon Size (bp) | Primer Efficiency E (%) | (r2) | Reference |
|---|---|---|---|---|---|---|---|---|---|---|---|
| Q09 | *ACT* | actin gene Ac2 | 108204443 | X17525.1 | F | CACACGGTGCCAATTTATGAA | 40 | 73 | 96,18 | 1,000 | Campos et al. 2015 |
| | | | | | R | GATCACGGCCAGCAAGGT | 41 | | | | |
| Q100 | *MYB90-like* | transcription factor MYB90-like | 108221186 | XM_017395082.1 | F | AAGGCACAAGCCTATCCTGC | 42 | 124 | 96,52 | 1,000 | |
| | | | | | R | TGGTCATTCGGTGCCAGTTT | 43 | | | | |
| Q19 | *EGL1* | transcription factor EGL1 | 108210744 | XM_017382138.1 | F | TGGAGATATAAAGACGCGAAAAAC | 44 | 112 | 107,12 | 0,985 | |
| | | | | | R | GGCATCCAGGAGGGACTCA | 45 | | | | |
| Q94 | *PAL3* | phenylalanine ammonia-lyase | 108217754 | AB089813.1 | F | CTGGCATGGCCTCTATGGTACT | 46 | 145 | 99,68 | 0,999 | Xu et al. 2014 |
| | | | | | R | TGTCCTGGATGGTGCTTCAACT | 47 | | | | |
| Q83 | *C4H-1* | cinammate 4-hydroxylase 1 | 108223289 | KM359961 | F | GTGGAGGCCAACGGAAATG | 48 | 123 | 99,61 | 1,000 | |
| | | | | | R | CGTCCGATTGTGATACCGAGA | 49 | | | | |
| Q85 | *4CL1* | 4-coumarate--CoA ligase 1 | 108227923 | KM359963 | F | AAACACCTGCCGTTACACTCG | 50 | 189 | 101,56 | 0,987 | |
| | | | | | R | CGGAAGCAAGATCATCATCGTAT | 51 | | | | |
| Q95 | *CHS1* | chalcone synthase 1 | 108200622 | AJ006779.1 | F | TTCCACCTTCTCAAAGATGTTCC | 52 | 162 | 101,16 | 1,000 | |
| | | | | | R | GCTCAACTCTGTTTCAACTTGGTC | 53 | | | | |
| Q89 | *CHI1* | chalcone-flavonone isomerase 1 | 108197475 | KM359964 | F | TCCTGCCACGGTCAAACCT | 54 | 148 | 97,21 | 0,999 | |
| | | | | | R | AAGAGCGAGCGACGGAATC | 55 | | | | |
| Q90 | *F3H1* | flavanone 3-hydroxylase | 108213382 | AF184270.1 | F | GAGTACAGTGAGAAGCTGATGGGTC | 56 | 149 | 104,18 | 0,999 | |
| | | | | | R | GGTTGAGGGCACTTGGGATAG | 57 | | | | |
| Q91 | *F3'H1* | flavonoid 3'-monooxygenase 1 | 108216209 | KM359965 | F | TTGAGGATGGTGAAGGTGGGA | 58 | 135 | 92,85 | 0,998 | |
| | | | | | R | CTTTTGGGCGACGCAGAAC | 59 | | | | |
| Q92 | *DFR1* | dihydroflavonol 4-reductase | 108224780 | AF184271.1 | F | GTTATCAAGCCTACCGTACAGGG | 60 | 99 | 97,88 | 0,998 | |
| | | | | | R | AGTTCCAGCAGACGAAGTGTAAAT | 61 | | | | |
| Q93 | *LDOX1* | leucoanthocyanidin dioxygenase | 108209615 | AF184273.1 | F | AGGTGCCCACAGTCGACATAGC | 62 | 167 | 97,90 | 0,999 | |
| | | | | | R | CGCCTGTCCAGCCACTCTAA | 63 | | | | |
| Q101 | *UCGalT1* | UDP-galactose:cyanidin 3-O-galactosyl-transferase 1 | 108213096 | KP319022 | F | ATTCGAGGAACTAGACCCTGACC | 64 | 162 | 97,15 | 0,998 | Xu et al. 2016 |
| | | | | | R | GCCACAGACTTAGGATTACGCTTG | 65 | | | | |

Fig. 3

| pTM90-E1 transformants or cultivar* | Relative peak area in HPLC chromatograms (%) | | | | | TMA mg/g FW |
|---|---|---|---|---|---|---|
| | C3xg | C3x(G)g | C3x(CG)g | C3x(FG)g | C3x(SG)g | |
| | 581 (m/z) | 743 (m/z) | 889 (m/z) | 919 (m/z) | 949 (m/z) | |
| L1 | 0,00 | 0,65 | 0,45 | 34,96 | 62,09 | 2,03 |
| L2 | 0,00 | 0,52 | 0,54 | 38,99 | 57,97 | 1,80 |
| DP | 15,34 | 3,94 | 6,18 | 70,58 | 1,72 | 2,20 |
| NB | 18,19 | 4,11 | 17,80 | 51,66 | 6,43 | 2,38 |
| Dan | 0,00 | 0,00 | 0,00 | 0,00 | 0,00 | 0,00 |

Fig. 4

| pTM90-E1 transformants or cultivar* | SingleMS and MS/MS isolated anthocyanins (mg/g FW) | | | | | | | | | | TSA mg g-1 (FW) |
|---|---|---|---|---|---|---|---|---|---|---|---|
| | C3xg | | C3x(G)g | | C3x(CG)g | | C3x(FG)g | | C3x(SG)g | | |
| m/z | 581 (m/z) | % | 743 (m/z) | % | 889 (m/z) | % | 919 (m/z) | % | 949 (m/z) | % | |
| L1 | 0,00 | | 0,00 | | 0,00 | | 0.83±0.09 | 33.88 | 1.62±0.21 | 66.12 | 2.45±0.39 |
| L2 | 0,00 | | 0,00 | | 0,00 | | 0.51±0.11 | 33.75 | 1.01±0.23 | 66.89 | 1.51±0.33 |
| L3 | 0.14±0.02 | 22.95 | 0.01±0.01 | 1.64 | 0,00 | | 0.27±0.02 | 44.26 | 0.19±0.02 | 31.15 | 0.61±0.12 |
| L4 | 0,00 | | 0,00 | | 0,00 | | 0.29±0.02 | 40.28 | 0.43±0.21 | 59.72 | 0.72±0.15 |
| L5 | 0,00 | | 0,00 | | 0,00 | | 0.23±0.03 | 31.51 | 0.51±0.23 | 69.86 | 0.73±0.18 |
| L6 | 0.05±0.02 | 5.26 | 0,00 | | 0,00 | | 0.30±0.11 | 31.58 | 0.60±0.29 | 63.16 | 0.95±0.21 |
| NB | 1.49±0.31 | 33.48 | 0.15±0.05 | 3.37 | 0.58±0.31 | 13.03 | 1.30±0.27 | 29.21 | 0.92±0.46 | 20.67 | 4.45±0.53 |
| Dan | 0,00 | | 0,00 | | 0,00 | | 0,00 | | 0,00 | | 0,00 |

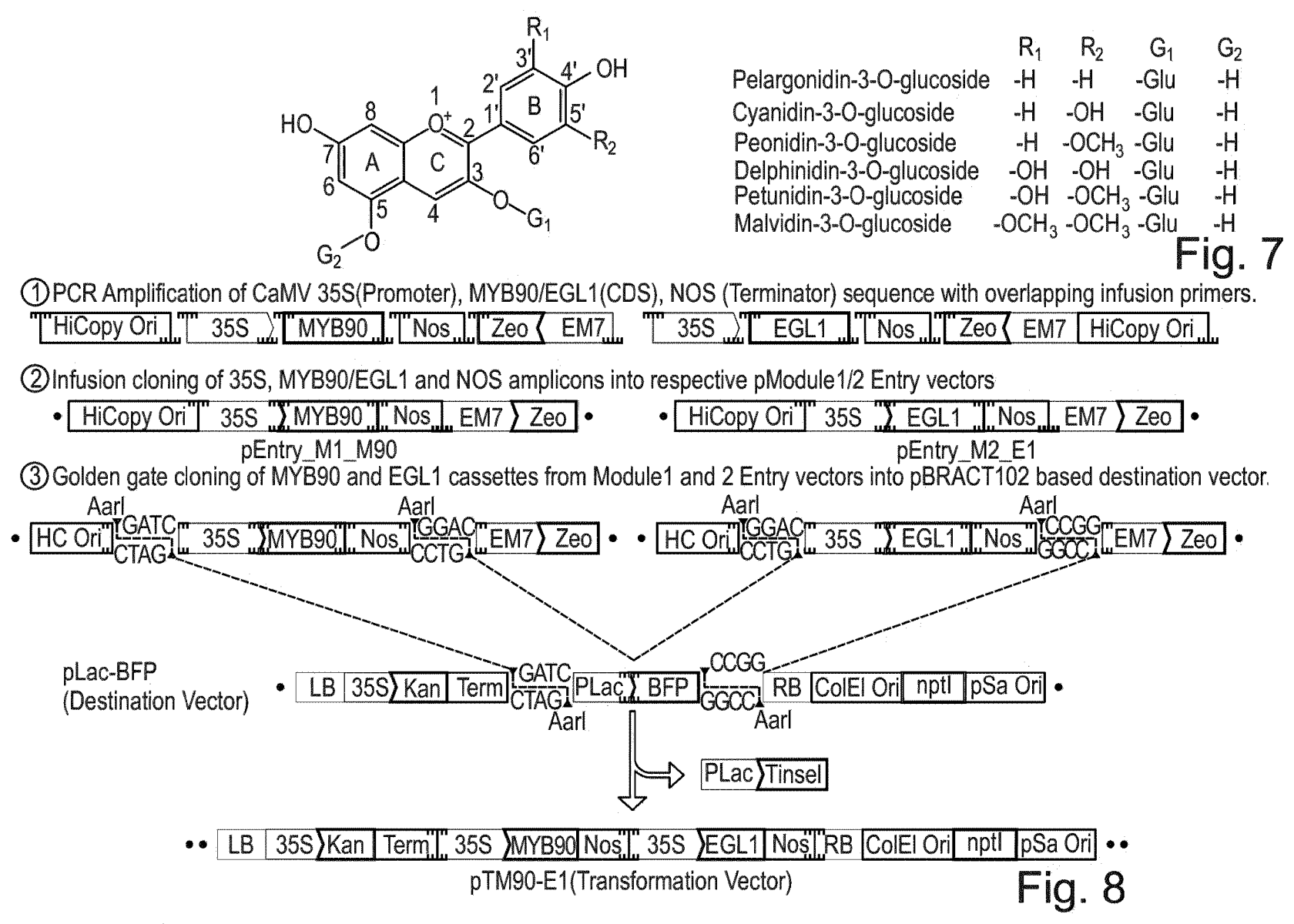

| | $R_1$ | $R_2$ | $G_1$ | $G_2$ |
| --- | --- | --- | --- | --- |
| Pelargonidin-3-O-glucoside | -H | -H | -Glu | -H |
| Cyanidin-3-O-glucoside | -H | -OH | -Glu | -H |
| Peonidin-3-O-glucoside | -H | $-OCH_3$ | -Glu | -H |
| Delphinidin-3-O-glucoside | -OH | -OH | -Glu | -H |
| Petunidin-3-O-glucoside | -OH | $-OCH_3$ | -Glu | -H |
| Malvidin-3-O-glucoside | $-OCH_3$ | $-OCH_3$ | -Glu | -H |

Fig. 7

① PCR Amplification of CaMV 35S(Promoter), MYB90/EGL1(CDS), NOS (Terminator) sequence with overlapping infusion primers.

HiCopy Ori | 35S | MYB90 | Nos | Zeo | EM7    35S | EGL1 | Nos | Zeo | EM7 | HiCopy Ori ② Infusion cloning of 35S, MYB90/EGL1 and NOS amplicons into respective pModule1/2 Entry vectors HiCopy Ori | 35S | MYB90 | Nos | EM7 | Zeo    HiCopy Ori | 35S | EGL1 | Nos | EM7 | Zeo pEntry_M1_M90    pEntry_M2_E1

③ Golden gate cloning of MYB90 and EGL1 cassettes from Module1 and 2 Entry vectors into pBRACT102 based destination vector.

AarI AarI AarI AarI

HC Ori | GATC CTAG | 35S | MYB90 | Nos | GGAC CCTG | EM7 | Zeo    HC Ori | GGAC CCTG | 35S | EGL1 | Nos | CCGG GGCC | EM7 | Zeo pLac-BFP (Destination Vector)

LB | 35S | Kan | Term | GATC CTAG | PLac | BFP | CCGG GGCC | RB | ColEI Ori | nptI | pSa Ori AarI AarI PLac | Tinsel LB | 35S | Kan | Term | 35S | MYB90 | Nos | 35S | EGL1 | Nos | RB | ColEI Ori | nptI | pSa Ori pTM90-E1(Transformation Vector)

Fig. 8

| Vector | Component | Forward/Reverse Primer | Primer Sequence (5'-3') | SEQ ID NO |
|---|---|---|---|---|
| pRos1 | 35Sx2 | pBract102_XhoI_35Sx2_Fw | TTGATCCCC**CTCGAG**ATCCGTCAACATG | 66 |
| | | AmRosea1_NcoI_35Sx2_ Rv | CAATTCTTTT**CCATGG**TCGTCCTCTCCAAATG | 67 |
| | AmRosea1 | 35Sx2_NcoI_AmROSEA1_Fw | GAGGACGA**CCATGG**AAAAGAATTGTCGTGGAGTG | 68 |
| | | NOS_ HindIII_ AmROSEA1_ Rv | GGGAAATTC**AAGCTT**TTAATTTCCAATTTGTTGGGCCT | 69 |
| | NOS | AmRosea1_HindIII_NOS_Fw | TGGAAATTAA**AAGCTT**GAATTTCCCCGATCGTTC | 70 |
| | | pBract102_ EcoRI_ NOS_ Rv | GGCTGCAG**GAATTC**CGATCTAGTAACATAGATG | 71 |
| pDel | 35Sx2 | pBract102_EcoRI_35Sx2_Fw | AAGCTTGATATC**GAATTC**GATCCGTCAACATG | 72 |
| | | AmDelila_NcoI_35Sx2_ Rv | TTGGAGAGGACGA**CCATGG**CTACTGGTATCCAAAACC | 73 |
| | AmDelila | 35Sx2_NcoI_AmDelila_Fw | TTGGAGAGGACGA**CCATGG**CTACTGGTATCCAAAACC | 74 |
| | | NOS_ XbaI_ AmDelila_ Rv | GGGAAATTC**TCTAGA**TCAAGACTTCATAATAACTTTCTGAAGAGC | 75 |
| | NOS | AmDelila_XbaI_NOS_Fw | GTTATTATGAAGTCTTGA**TCTAGA**GAATTTCCCCGATCGTTC | 76 |
| | | pBract102_ SacI_ NOS_ Rv | GAACAAAAGCTG**GAGCTC**CCGATCTAGTAACATAGATG | 77 |
| pRD | 35Sx2:AmDelila:NOS | NOS_PstI_35Sx2_Fw | CTAGATCGGAATTC**CTGCAG**GATCCGTCAACAT | 78 |
| | | pBract102_PstI_ NOS _Rv | GATCCCCCGGG**CTGCAG**GAATTCCGATCTAGT | 79 |

Fig. 13

| | Germination Medium | Co-culture Medium | Selection Medium 1 | Selection Medium 2 | Regeneration Medium |
|---|---|---|---|---|---|
| B5 (Macro, micro, vit) | 3.2g | 3.2 g | 3.2 g | 3.2 g | 3.2g |
| 2,4-D | | 1 mg | 1 mg | 1 mg | |
| CuSO4 | | | 1.25 mg | 1.25 mg | 1.25 mg |
| Sucrose | 30g | 30 g | 30 g | 30 g | 30g |
| Timentin | | | 300 mg | 300 mg | |
| Kanamycin | | | 20 mg | 100 mg | 100 mg |
| Gelzan™ | 2.5g | 2.5g | 2.5g | 2.5g | 2.5 g |
| pH | 5.8 | 5.8 | 5.8 | 5.8 | 5.8 |

Fig. 14

| pRD transformants or cultivar* | Relative peak area in HPLC chromatograms (%) | | | | | | TMA mg $g^{-1}$ (FW) |
|---|---|---|---|---|---|---|---|
| | C3xg | C3x(G)g | C3x(CG)g | C3x(FG)g | C3x(SG)g | P3x(SG)g | |
| | 581(m/z) | 743 (m/z) | 889 (m/z) | 919 (m/z) | 949 (m/z) | 963 (m/z) | |
| L22 | | 1.83 | 4.93 | 3.32 | **87.69** | 2.30 | 2.24 |
| L23 | 1.97 | 5.63 | 4.77 | 1.93 | **82.54** | 2.33 | 1.73 |
| L24 | | 4.34 | 4.30 | 3.11 | **82.99** | 2.00 | 1.24 |
| L25 | | 4.06 | 6.90 | 3.03 | **82.24** | 1.92 | 2.45 |
| L26 | 1.38 | 3.93 | 5.81 | 2.60 | **82.99** | 2.43 | 1.65 |
| L28 | 1.66 | 3.77 | 8.94 | 4.25 | **77.89** | 2.46 | 1.98 |
| DP (Control) | 15.34 | 3.94 | 6.18 | **70.58** | 1,72 | 0.22 | 2.19 |

Fig. 15

| pRD transformants or cultivar* | Anthocyanin content detected by MS and MS/MS (mg g$^{-1}$) | | | | | | | | TSA mg g$^{-1}$ (DW) |
|---|---|---|---|---|---|---|---|---|---|
| | C3x(G)g | | C3x(FG)g | | C3x(SG)g | | P3x(SG)g | | |
| | 743 (m/z) | (%) | 919 (m/z) | (%) | 949 (m/z) | (%) | 963 (m/z) | (%) | |
| L22 | **3.81** ±0.15 | **15.6** | 0.18 ±0.04 | 0.7 | **18.27** ±0.58 | **76.0** | 1.31 ±0.14 | 5.4 | 24.44 ±1.00 |
| L23 | 0.35 ±0.42 | 3.6 | 0.06 ±0.01 | 0.6 | **9.46** ±0.57 | **96.7** | 0.04 ±0.26 | 0.4 | 9.78 ±1.57 |
| L24 | 0.02 ±0.01 | 0.3 | 0.13 ±0.02 | 2.2 | **5.68** ±0.10 | **97.6** | 0.05 ±0.01 | 0.9 | 5.82 ±0.15 |
| L25 | 2.62 ±0.01 | 13.7 | 0.17 ±0.01 | 0.9 | **15.00** ±0.15 | **78.5** | 0.78 ±0.01 | 4.1 | 19.11 ±0.20 |
| L26 | 0.51 ±0.01 | 2.4 | 0.20 ±0.02 | 0.9 | **18.21** ±0.30 | **86.5** | 1.62 ±0.10 | 7.7 | 21.06 ±0.43 |
| L28 | **6.98** ±0.65 | **15.7** | 0.19 ±0.17 | 0.4 | **31.30** ±7.32 | **70.5** | **3.25** ±1.04 | **7.3** | 44.38 ±10.67 |
| DP (Control) | 1.64 ±0.94 | 6.9 | **20.54** ±1.17 | **86.2** | 1.91±0.16 | 8.0 | 0.00 ±0.00 | 0.0 | 23.82 ±2.28 |
Fig. 16
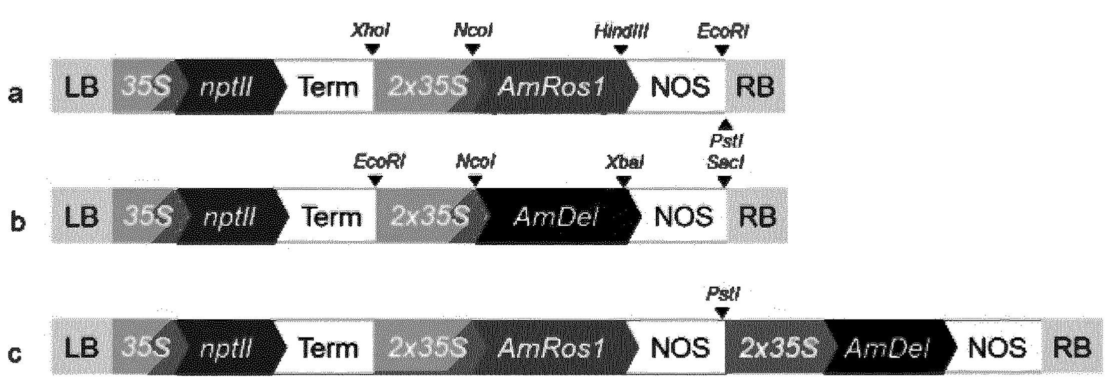
Fig. 17
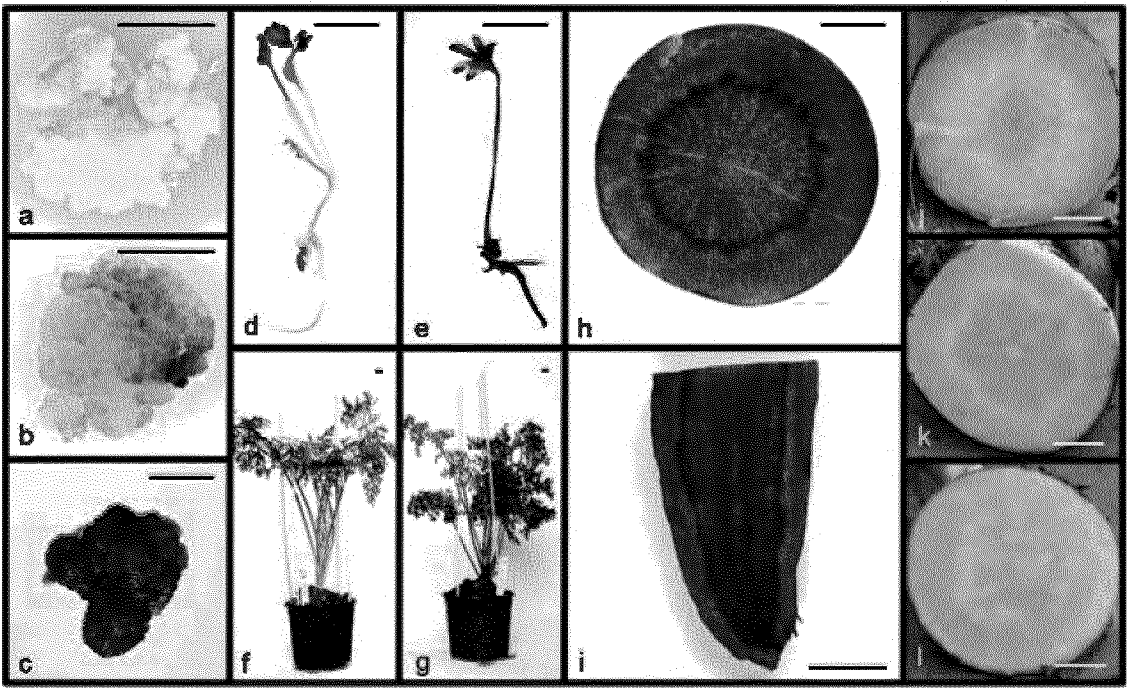
Fig. 18

SEQUENCE LISTING

```
<160> NUMBER OF SEQ ID NOS: 79

<210> SEQ ID NO 1
<211> LENGTH: 882
<212> TYPE: DNA
<213> ORGANISM: Daucus carota

<400> SEQUENCE: 1

atgagctatt ccaagggcat gaagagtgct aacacagctt caaagctgcg aaagggtgca      60

tgggattttg aggaagacac tcttctccga aaatgcattg acaagtatgg agaaggaaag     120

tggcaccttg ttccgcagag agctgggttg aatagatgca gaaaaagttg tagactaagg     180

tggcttaact atctgaggcc taccatcaag agaggagaat tcagtgctga tgaagtggat     240

cttatgatgc gccttcacag gcttctggga aaccgatggt cgctgattgg aggaagactg     300

ccgggaagaa cagctaatga tgttaagaac tactggaaca ccaacattca aaagaaactc     360

actactcgca gcaacaagaa agacgtggcg ataagagaag agcttcttca aagaaaacaa     420

tacagtagta ttgctgcaac tagtactggt gctactgtta taaagcctct tccccggact     480

ttatccaaag gcacaagcct atcctgctat gatcttaatc ccaagaaacc cgttcgtaac     540

ttgaatgaca cactacacaa caacattaac aacaaggcat catcaccagc aaaactggca     600

ccgaatgacc aaggcaagga gaccctgcca ctggatgaag atgtcataga gtggtggaag     660

aatttgtttg aggaaataaa cattaatggt caagagcaag attactcaga cggactgttg     720

atggcatcct cgagcggttc agataatgtg catgctgaca gagacttcgt gtggaagaca     780

gatgaatcaa ccgcagcagc aatggaattg tcagaagatg gtttgtgtga catttggaat     840
```

-continued cttctagact catcagacca tgtccgattg agtcggttat aa 882

<210> SEQ ID NO 2
<211> LENGTH: 1785
<212> TYPE: DNA
<213> ORGANISM: Daucus carota

<400> SEQUENCE: 2
atggcagaga tcctgagaaa gcagctggct cttgctgtta agaagattca gtggagctat 60
gcaattttct gggccatttc atcatcacag aatggggtat tggagtggga tgatgggtac 120
tacaatggag atataaagac gcgaaaaaca gttcaagcag aacagttaaa tgttgatcag 180
cttggattac aaaggactga gcaattgaga gaactttatg agtccctcct ggatgccgaa 240
aacaacagac actctgcaag gccttctgct gcattatctc ctgaagatct tactgatacc 300
gagtggtatt tcttgatatg catgtcgttt gtgttcaata gtggccaagg gttgcctggg 360
agatcattag caaaaaatca aaccacttgg ttgtgcaatg caaattatgc agatagcaaa 420
gtgtttaatc gtgttctgct tgcaaagagt gcattgattc agacagttgt atgctttcca 480
tattcagatg gcgtaattga aattggtaca actgacctgg tttcagagga tcctagtata 540
gtccagtaca taaaatcttt cttggggact ccaggggcaa tttttgagag tgttgctgat 600
gccgatctga acccagatac tgaatgggaa aaaggcaaca tgtgctcctc aaatggtagt 660
ttagaagaag ttgagccaaa ttatcaggca aaggaatcac tagtggctga acgccttgat 720
gatggcacct ctcagcaaaa aagctggcaa ttaatggatg gtgaaatcag taacactttc 780
ctcgactctg gagattccag tgactgtata tccgaaacct ttatagcccc tgaaaagact 840
gtccctcaac aagataaata taacaaggtt gatgaaaacc gtctacttga gcttcaaggt 900
tccaaggata tggaactgac ttcagttgag attctggaag atgatttcaa ctaccaaggt 960
attgtgtcca cccttctgaa gacttcccac caattgatta tgggaccatg tttcaaaagc 1020
agtataaaag attcatgctt tgttagatgg aaaaaaggca gatccccgtg taaatacaag 1080
tcaggtggaa cttctcaaag attgctgaaa aaggtactgt acgaagttcc tgtaaagcat 1140
aacgatggta aaataaggaa accagagagt tttgaatctg atacaaacca tgcaccagaa 1200
gagagaaggc aaagagaaaa gatgcaggaa aagtttatga ttcttagatc gatagtacct 1260
tcaactggca aggttgacaa tgtgtcattg cttgatgaga ctatagaata ccttagaaat 1320
cttgagaaaa gggttgaggg attagaatct cagaaagagc ttgtagacgt agaagcaaga 1380
aggggaaaga gaatttttaa tgtcatagag agtacttctg ataactatgg cgacatgaga 1440
gtaagttaca gcaagaagca ggtgctgaat aagaggaagg gttctggtac caacactatg 1500
aatgctataa accaattgca tcaggaagac aataagactg acgacgtgaa agtttctaaa 1560
acagggaagg gcattgtcat agagattgaa tgtccttggc gagaggagtt gtttgtagat 1620
atcatgggcg caataaacaa ccttcatttg gattctcact cggttcaatc ttccaagatt 1680
gatggaaacc tttctttgac gattaactct aaggtgaaag gatcaactat gccatctgta 1740
aatataataa gacaagcact tcaacgagtt accagaaagt cctaa 1785

<210> SEQ ID NO 3
<211> LENGTH: 436
<212> TYPE: DNA
<213> ORGANISM: Cauliflower mosaic virus

<400> SEQUENCE: 3

-continued

```
ctcgagatcc gtcaacatgg tggagcacga cactctcgtc tactccaaga atatcaaaga     60

tacagtctca gaagaccaaa gggctattga gacttttcaa caaagggtaa tatcgggaaa    120

cctcctcgga ttccattgcc cagctatctg tcacttcatc aaaaggacag tagaaaagga    180

aggtggcacc tacaaatgcc atcattgcga taaaggaaag gctatcgttc aagatgcctc    240

tgccgacagt ggtcccaaag atggaccccc acccacgagg agcatcgtgg aaaaagaaga    300

cgttccaacc acgtcttcaa agcaagtgga ttgatgtgat atctccactg acgtaaggga    360

tgacgcacaa tcccactatc cttcgcaaga cccttcctct atataaggaa gttcatttca    420

tttggagagg acgacc                                                    436
```

```
<210> SEQ ID NO 4
<211> LENGTH: 1422
<212> TYPE: DNA
<213> ORGANISM: Daucus carota

<400> SEQUENCE: 4

atgagccctg tatatcaaga ctccaaaaag gatcttgttc atatcttact tgtgtctttc     60

ataggacaag gccatgtcaa ccctttactc agactaggaa acctccttgc ttcatcaggt    120

ttccttgtca ccttctcttc ctgttcggaa gtcggaaatt ccatgcgcaa ggctaacaac    180

aacatcgatg aactcgttcc agttggcgat gggatgatca ggtttgagtt ttttgatgat    240

ggattacccg agagtgatcc acgacgccat gatctcgact tctacatgcc tcaccttgag    300

ttgcatggta aagaggcagt cactggcatt gtcaagaaac acgaaaaaga agggcgtccg    360

gtgtcatgca tcatcaacaa tcctttcatt ccatgggttt ctgacatcgc ggaggcctta    420

agcattcgta atgcagtgct ttgggtacag tcctgtgctt gtttttcagc ttattaccat    480

taccacaata agttgtcaca gtttccctcc gaatctgaac ccgaaatcga tgtccaactg    540

ccatctatgc ctctgttaaa acatgatgaa atcccaagtt tcttacaccc ttcaactcct    600

tatccagcct taagaagaac aattctagcc caattcaaga acttgtcaaa accattctgt    660

gtactagtag aaacatttca agaactcgaa agtgaagtca ttgattacat gtccaaactc    720

tgccccatca aggccatcgg ccctctattc aagaacccga aatctcaact ttctaacatc    780

caaggcgatt gcttgaagcc cgtcgatgac tgcatcgatt tcctgaactc caaaagcccc    840

tcatccgttg tctacatctc tttcggcagt gttatctcaa tgaaccaaaa acaaacaaat    900

gaacttgctc aaggtctttt aaactccgga gtttcttttc tctgggtttt taggccaccc    960

cttccaggtt tcgacgtagc tgtactaccc gaaaaattcc tggaagcagc tggtgacaag   1020

ggaaaagtag tgcagtggtg ttcacagaaa caagtcctgg caagtcctgc agtggcttgt   1080

tttctgacac attgcggatg gaattcgacg ttagaggcct taacaactgg tgtccctgtg   1140

ataacctacc ctgcatgggg tgatcaagtc actaatgcta agtttttagt tgatgtgtta   1200

aaagtgggag tcaggttaag tagagggaac caatctaaaa aaaatgtcat ttccagggac   1260

gatatcgaaa aatctttaag agaagctacc attggggaaa atgcagcaga gattaaaagg   1320

aatgcattga agtggaagga ggcggcagag gacgcggtgg cagagggcgg ttcttctgat   1380

cggaacttga aagagtttgt ggataagctg atgatgaact ga                       1422
```

```
<210> SEQ ID NO 5
<211> LENGTH: 293
<212> TYPE: PRT
<213> ORGANISM: Daucus carota

<400> SEQUENCE: 5
```

```
Met Ser Tyr Ser Lys Gly Met Lys Ser Ala Asn Thr Ala Ser Lys Leu
1               5                   10                  15

Arg Lys Gly Ala Trp Asp Phe Glu Glu Asp Thr Leu Leu Arg Lys Cys
            20                  25                  30

Ile Asp Lys Tyr Gly Glu Gly Lys Trp His Leu Val Pro Gln Arg Ala
        35                  40                  45

Gly Leu Asn Arg Cys Arg Lys Ser Cys Arg Leu Arg Trp Leu Asn Tyr
    50                  55                  60

Leu Arg Pro Thr Ile Lys Arg Gly Glu Phe Ser Ala Asp Glu Val Asp
65                  70                  75                  80

Leu Met Met Arg Leu His Arg Leu Leu Gly Asn Arg Trp Ser Leu Ile
                85                  90                  95

Gly Gly Arg Leu Pro Gly Arg Thr Ala Asn Asp Val Lys Asn Tyr Trp
            100                 105                 110

Asn Thr Asn Ile Gln Lys Lys Leu Thr Thr Arg Ser Asn Lys Lys Asp
        115                 120                 125

Val Ala Ile Arg Glu Glu Leu Leu Gln Arg Lys Gln Tyr Ser Ser Ile
    130                 135                 140

Ala Ala Thr Ser Thr Gly Ala Thr Val Ile Lys Pro Leu Pro Arg Thr
145                 150                 155                 160

Leu Ser Lys Gly Thr Ser Leu Ser Cys Tyr Asp Leu Asn Pro Lys Lys
                165                 170                 175

Pro Val Arg Asn Leu Asn Asp Thr Leu His Asn Asn Ile Asn Asn Lys
            180                 185                 190

Ala Ser Ser Pro Ala Lys Leu Ala Pro Asn Asp Gln Gly Lys Glu Thr
        195                 200                 205

Leu Pro Leu Asp Glu Asp Val Ile Glu Trp Trp Lys Asn Leu Phe Glu
    210                 215                 220

Glu Ile Asn Ile Asn Gly Gln Glu Gln Asp Tyr Ser Asp Gly Leu Leu
225                 230                 235                 240

Met Ala Ser Ser Ser Gly Ser Asp Asn Val His Ala Asp Arg Asp Phe
                245                 250                 255

Val Trp Lys Thr Asp Glu Ser Thr Ala Ala Ala Met Glu Leu Ser Glu
            260                 265                 270

Asp Gly Leu Cys Asp Ile Trp Asn Leu Leu Asp Ser Ser Asp His Val
        275                 280                 285

Arg Leu Ser Arg Leu
    290
```

<210> SEQ ID NO 6
<211> LENGTH: 594
<212> TYPE: PRT
<213> ORGANISM: Daucus carota

<400> SEQUENCE: 6

```
Met Ala Glu Ile Leu Arg Lys Gln Leu Ala Leu Ala Val Lys Lys Ile
1               5                   10                  15

Gln Trp Ser Tyr Ala Ile Phe Trp Ala Ile Ser Ser Ser Gln Asn Gly
            20                  25                  30

Val Leu Glu Trp Asp Asp Gly Tyr Tyr Asn Gly Asp Ile Lys Thr Arg
        35                  40                  45

Lys Thr Val Gln Ala Glu Gln Leu Asn Val Asp Gln Leu Gly Leu Gln
    50                  55                  60

Arg Thr Glu Gln Leu Arg Glu Leu Tyr Glu Ser Leu Leu Asp Ala Glu
```

-continued

```
65                  70                  75                  80

Asn Asn Arg His Ser Ala Arg Pro Ser Ala Ala Leu Ser Pro Glu Asp
                85                  90                  95

Leu Thr Asp Thr Glu Trp Tyr Phe Leu Ile Cys Met Ser Phe Val Phe
            100                 105                 110

Asn Ser Gly Gln Gly Leu Pro Gly Arg Ser Leu Ala Lys Asn Gln Thr
        115                 120                 125

Thr Trp Leu Cys Asn Ala Asn Tyr Ala Asp Ser Lys Val Phe Asn Arg
    130                 135                 140

Val Leu Leu Ala Lys Ser Ala Leu Ile Gln Thr Val Val Cys Phe Pro
145                 150                 155                 160

Tyr Ser Asp Gly Val Ile Glu Ile Gly Thr Thr Asp Leu Val Ser Glu
                165                 170                 175

Asp Pro Ser Ile Val Gln Tyr Ile Lys Ser Phe Leu Gly Thr Pro Gly
            180                 185                 190

Ala Ile Phe Glu Ser Val Ala Asp Ala Asp Leu Asn Pro Asp Thr Glu
        195                 200                 205

Trp Glu Lys Gly Asn Met Cys Ser Ser Asn Gly Ser Leu Glu Glu Val
    210                 215                 220

Glu Pro Asn Tyr Gln Ala Lys Glu Ser Leu Val Ala Glu Arg Leu Asp
225                 230                 235                 240

Asp Gly Thr Ser Gln Gln Lys Ser Trp Gln Leu Met Asp Gly Glu Ile
                245                 250                 255

Ser Asn Thr Phe Leu Asp Ser Gly Asp Ser Ser Asp Cys Ile Ser Glu
            260                 265                 270

Thr Phe Ile Ala Pro Glu Lys Thr Val Pro Gln Gln Asp Lys Tyr Asn
        275                 280                 285

Lys Val Asp Glu Asn Arg Leu Leu Glu Leu Gln Gly Ser Lys Asp Met
    290                 295                 300

Glu Leu Thr Ser Val Glu Ile Leu Glu Asp Asp Phe Asn Tyr Gln Gly
305                 310                 315                 320

Ile Val Ser Thr Leu Leu Lys Thr Ser His Gln Leu Ile Met Gly Pro
                325                 330                 335

Cys Phe Lys Ser Ser Ile Lys Asp Ser Cys Phe Val Arg Trp Lys Lys
            340                 345                 350

Gly Arg Ser Pro Cys Lys Tyr Lys Ser Gly Gly Thr Ser Gln Arg Leu
        355                 360                 365

Leu Lys Lys Val Leu Tyr Glu Val Pro Val Lys His Asn Asp Gly Lys
    370                 375                 380

Ile Arg Lys Pro Glu Ser Phe Glu Ser Asp Thr Asn His Ala Pro Glu
385                 390                 395                 400

Glu Arg Arg Gln Arg Glu Lys Met Gln Glu Lys Phe Met Ile Leu Arg
                405                 410                 415

Ser Ile Val Pro Ser Thr Gly Lys Val Asp Asn Val Ser Leu Leu Asp
            420                 425                 430

Glu Thr Ile Glu Tyr Leu Arg Asn Leu Glu Lys Arg Val Glu Gly Leu
        435                 440                 445

Glu Ser Gln Lys Glu Leu Val Asp Val Glu Ala Arg Arg Gly Lys Arg
    450                 455                 460

Ile Phe Asn Val Ile Glu Ser Thr Ser Asp Asn Tyr Gly Asp Met Arg
465                 470                 475                 480

Val Ser Tyr Ser Lys Lys Gln Val Leu Asn Lys Arg Lys Gly Ser Gly
                485                 490                 495
```

```
Thr Asn Thr Met Asn Ala Ile Asn Gln Leu His Gln Glu Asp Asn Lys
            500                 505                 510

Thr Asp Asp Val Lys Val Ser Lys Thr Gly Lys Gly Ile Val Ile Glu
        515                 520                 525

Ile Glu Cys Pro Trp Arg Glu Glu Leu Phe Val Asp Ile Met Gly Ala
    530                 535                 540

Ile Asn Asn Leu His Leu Asp Ser His Ser Val Gln Ser Ser Lys Ile
545                 550                 555                 560

Asp Gly Asn Leu Ser Leu Thr Ile Asn Ser Lys Val Lys Gly Ser Thr
                565                 570                 575

Met Pro Ser Val Asn Ile Ile Arg Gln Ala Leu Gln Arg Val Thr Arg
            580                 585                 590

Lys Ser


<210> SEQ ID NO 7
<211> LENGTH: 473
<212> TYPE: PRT
<213> ORGANISM: Daucus carota

<400> SEQUENCE: 7

Met Ser Pro Val Tyr Gln Asp Ser Lys Lys Asp Leu Val His Ile Leu
1               5                   10                  15

Leu Val Ser Phe Ile Gly Gln Gly His Val Asn Pro Leu Leu Arg Leu
            20                  25                  30

Gly Asn Leu Leu Ala Ser Ser Gly Phe Leu Val Thr Phe Ser Ser Cys
        35                  40                  45

Ser Glu Val Gly Asn Ser Met Arg Lys Ala Asn Asn Asn Ile Asp Glu
    50                  55                  60

Leu Val Pro Val Gly Asp Gly Met Ile Arg Phe Glu Phe Phe Asp Asp
65                  70                  75                  80

Gly Leu Pro Glu Ser Asp Pro Arg Arg His Asp Leu Asp Phe Tyr Met
                85                  90                  95

Pro His Leu Glu Leu His Gly Lys Glu Ala Val Thr Gly Ile Val Lys
            100                 105                 110

Lys His Glu Lys Glu Gly Arg Pro Val Ser Cys Ile Ile Asn Asn Pro
        115                 120                 125

Phe Ile Pro Trp Val Ser Asp Ile Ala Glu Ala Leu Ser Ile Arg Asn
    130                 135                 140

Ala Val Leu Trp Val Gln Ser Cys Ala Cys Phe Ser Ala Tyr Tyr His
145                 150                 155                 160

Tyr His Asn Lys Leu Ser Gln Phe Pro Ser Glu Ser Glu Pro Glu Ile
                165                 170                 175

Asp Val Gln Leu Pro Ser Met Pro Leu Leu Lys His Asp Glu Ile Pro
            180                 185                 190

Ser Phe Leu His Pro Ser Thr Pro Tyr Pro Ala Leu Arg Arg Thr Ile
        195                 200                 205

Leu Ala Gln Phe Lys Asn Leu Ser Lys Pro Phe Cys Val Leu Val Glu
    210                 215                 220

Thr Phe Gln Glu Leu Glu Ser Glu Val Ile Asp Tyr Met Ser Lys Leu
225                 230                 235                 240

Cys Pro Ile Lys Ala Ile Gly Pro Leu Phe Lys Asn Pro Lys Ser Gln
                245                 250                 255

Leu Ser Asn Ile Gln Gly Asp Cys Leu Lys Pro Val Asp Asp Cys Ile
            260                 265                 270
```

```
Asp Phe Leu Asn Ser Lys Ser Pro Ser Ser Val Val Tyr Ile Ser Phe
        275                 280                 285

Gly Ser Val Ile Ser Met Asn Gln Lys Gln Thr Asn Glu Leu Ala Gln
    290                 295                 300

Gly Leu Leu Asn Ser Gly Val Ser Phe Leu Trp Val Phe Arg Pro Pro
305                 310                 315                 320

Leu Pro Gly Phe Asp Val Ala Val Leu Pro Glu Lys Phe Leu Glu Ala
                325                 330                 335

Ala Gly Asp Lys Gly Lys Val Val Gln Trp Cys Ser Gln Lys Gln Val
            340                 345                 350

Leu Ala Ser Pro Ala Val Ala Cys Phe Leu Thr His Cys Gly Trp Asn
        355                 360                 365

Ser Thr Leu Glu Ala Leu Thr Thr Gly Val Pro Val Ile Thr Tyr Pro
    370                 375                 380

Ala Trp Gly Asp Gln Val Thr Asn Ala Lys Phe Leu Val Asp Val Leu
385                 390                 395                 400

Lys Val Gly Val Arg Leu Ser Arg Gly Asn Gln Ser Lys Lys Asn Val
                405                 410                 415

Ile Ser Arg Asp Asp Ile Glu Lys Ser Leu Arg Glu Ala Thr Ile Gly
            420                 425                 430

Glu Asn Ala Ala Glu Ile Lys Arg Asn Ala Leu Lys Trp Lys Glu Ala
        435                 440                 445

Ala Glu Asp Ala Val Ala Glu Gly Gly Ser Ser Asp Arg Asn Leu Lys
    450                 455                 460

Glu Phe Val Asp Lys Leu Met Met Asn
465                 470
```

<210> SEQ ID NO 8
<211> LENGTH: 23
<212> TYPE: DNA
<213> ORGANISM: Artificial Sequence
<220> FEATURE:
<223> OTHER INFORMATION: PCR primer

<400> SEQUENCE: 8
atgagctatt ccaagggcat gaa 23

<210> SEQ ID NO 9
<211> LENGTH: 22
<212> TYPE: DNA
<213> ORGANISM: Artificial Sequence
<220> FEATURE:
<223> OTHER INFORMATION: PCR primer

<400> SEQUENCE: 9
atggcagaga tcctgagaaa gc 22

<210> SEQ ID NO 10
<211> LENGTH: 26
<212> TYPE: DNA
<213> ORGANISM: Artificial Sequence
<220> FEATURE:
<223> OTHER INFORMATION: PCR primer

<400> SEQUENCE: 10
atgcattcaa agggtatgaa gattac 26

<210> SEQ ID NO 11
<211> LENGTH: 27

<212> TYPE: DNA
<213> ORGANISM: Artificial Sequence
<220> FEATURE:
<223> OTHER INFORMATION: PCR primer

<400> SEQUENCE: 11
tcaactatag tcctggttca gaagatc 27

<210> SEQ ID NO 12
<211> LENGTH: 27
<212> TYPE: DNA
<213> ORGANISM: Artificial Sequence
<220> FEATURE:
<223> OTHER INFORMATION: PCR primer

<400> SEQUENCE: 12
atgaagaatt gtaatccttt gaaggtg 27

<210> SEQ ID NO 13
<211> LENGTH: 32
<212> TYPE: DNA
<213> ORGANISM: Artificial Sequence
<220> FEATURE:
<223> OTHER INFORMATION: PCR primer

<400> SEQUENCE: 13
ttaaatgtaa tctaagttga gaagattcca aa 32

<210> SEQ ID NO 14
<211> LENGTH: 24
<212> TYPE: DNA
<213> ORGANISM: Artificial Sequence
<220> FEATURE:
<223> OTHER INFORMATION: PCR primer

<400> SEQUENCE: 14
ttataaccga ctcaatcgga catg 24

<210> SEQ ID NO 15
<211> LENGTH: 25
<212> TYPE: DNA
<213> ORGANISM: Artificial Sequence
<220> FEATURE:
<223> OTHER INFORMATION: PCR primer

<400> SEQUENCE: 15
ttaggacttt ctggtaactc gttga 25

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
atggcttcac caccacctta 20

<210> SEQ ID NO 17
<211> LENGTH: 27
<212> TYPE: DNA
<213> ORGANISM: Artificial Sequence
<220> FEATURE:
<223> OTHER INFORMATION: PCR primer

<400> SEQUENCE: 17
ctccatctga attaacctag taactca 27

<210> SEQ ID NO 18
<211> LENGTH: 50
<212> TYPE: DNA
<213> ORGANISM: Artificial Sequence
<220> FEATURE:
<223> OTHER INFORMATION: PCR primer

<400> SEQUENCE: 18
gaattctgat ctgagacccg gacgtgggca ggtggtgttg acaattaatc 50

<210> SEQ ID NO 19
<211> LENGTH: 37
<212> TYPE: DNA
<213> ORGANISM: Artificial Sequence
<220> FEATURE:
<223> OTHER INFORMATION: PCR primer

<400> SEQUENCE: 19
attttgccgt caaggcgata tcgacaaagg aaaaggg 37

<210> SEQ ID NO 20
<211> LENGTH: 34
<212> TYPE: DNA
<213> ORGANISM: Artificial Sequence
<220> FEATURE:
<223> OTHER INFORMATION: PCR primer

<400> SEQUENCE: 20
cttttccttt gtcgatatca aatcccttaa cgtg 34

<210> SEQ ID NO 21
<211> LENGTH: 48
<212> TYPE: DNA
<213> ORGANISM: Artificial Sequence
<220> FEATURE:
<223> OTHER INFORMATION: PCR primer

<400> SEQUENCE: 21
gatctcgagg atcatgagca ggtgcgcagg aaagaacatg tgagcaaa 48

<210> SEQ ID NO 22
<211> LENGTH: 33
<212> TYPE: DNA
<213> ORGANISM: Artificial Sequence
<220> FEATURE:
<223> OTHER INFORMATION: PCR primer

<400> SEQUENCE: 22
cacctgctca tgatcctcga gatccgtcaa cat 33

<210> SEQ ID NO 23
<211> LENGTH: 34
<212> TYPE: DNA
<213> ORGANISM: Artificial Sequence
<220> FEATURE:
<223> OTHER INFORMATION: PCR primer

<400> SEQUENCE: 23
ggtgcctgag accggtcgtc ctctccaaat gaaa 34

<210> SEQ ID NO 24
<211> LENGTH: 40
<212> TYPE: DNA
<213> ORGANISM: Artificial Sequence
<220> FEATURE:
<223> OTHER INFORMATION: PCR primer

<400> SEQUENCE: 24
gaccggtctc aggcaccatg agctattcca agggcatgaa 40

<210> SEQ ID NO 25
<211> LENGTH: 39
<212> TYPE: DNA
<213> ORGANISM: Artificial Sequence
<220> FEATURE:
<223> OTHER INFORMATION: PCR primer

<400> SEQUENCE: 25
gcttggtctc agtcgttata accgactcaa tcggacatg 39

<210> SEQ ID NO 26
<211> LENGTH: 33
<212> TYPE: DNA
<213> ORGANISM: Artificial Sequence
<220> FEATURE:
<223> OTHER INFORMATION: PCR primer

<400> SEQUENCE: 26
acgatcgggg aaattcaagc ttggtctcag tcg 33

<210> SEQ ID NO 27
<211> LENGTH: 39
<212> TYPE: DNA
<213> ORGANISM: Artificial Sequence
<220> FEATURE:
<223> OTHER INFORMATION: PCR primer

<400> SEQUENCE: 27
cacctgccca cgtccggaat tcgtcaccgg gcgatctag 39

<210> SEQ ID NO 28
<211> LENGTH: 38
<212> TYPE: DNA
<213> ORGANISM: Artificial Sequence
<220> FEATURE:
<223> OTHER INFORMATION: PCR primer

<400> SEQUENCE: 28
gaattccccg gtgacgcagg tggtgttgac aattaatc 38

<210> SEQ ID NO 29
<211> LENGTH: 46
<212> TYPE: DNA
<213> ORGANISM: Artificial Sequence
<220> FEATURE:
<223> OTHER INFORMATION: PCR primer

<400> SEQUENCE: 29
ctcgagggtc ccctggcagg tgcgcaggaa agaacatgtg agcaaa 46

<210> SEQ ID NO 30
<211> LENGTH: 34
<212> TYPE: DNA
<213> ORGANISM: Artificial Sequence
<220> FEATURE:
<223> OTHER INFORMATION: PCR primer

<400> SEQUENCE: 30
cacctgccag gggaccctcg agatccgtca acat 34

<210> SEQ ID NO 31
<211> LENGTH: 41
<212> TYPE: DNA
<213> ORGANISM: Artificial Sequence
<220> FEATURE:
<223> OTHER INFORMATION: PCR primer

<400> SEQUENCE: 31
ggtccaatga gacctctaga ggtcgtcctc tccaaatgaa a 41

<210> SEQ ID NO 32
<211> LENGTH: 45
<212> TYPE: DNA
<213> ORGANISM: Artificial Sequence
<220> FEATURE:
<223> OTHER INFORMATION: PCR primer

<400> SEQUENCE: 32
acctctagag gtctcattgg accatggcag agatcctgag aaagc 45

<210> SEQ ID NO 33
<211> LENGTH: 47
<212> TYPE: DNA
<213> ORGANISM: Artificial Sequence
<220> FEATURE:
<223> OTHER INFORMATION: PCR primer

<400> SEQUENCE: 33
attcggtctc accatagtcg acttaggact ttctggtaac tcgttga 47

<210> SEQ ID NO 34
<211> LENGTH: 34
<212> TYPE: DNA
<213> ORGANISM: Artificial Sequence
<220> FEATURE:
<223> OTHER INFORMATION: PCR primer

<400> SEQUENCE: 34
gtcgactatg gtgagaccga atttccccga tcgt 34

<210> SEQ ID NO 35
<211> LENGTH: 41
<212> TYPE: DNA
<213> ORGANISM: Artificial Sequence
<220> FEATURE:
<223> OTHER INFORMATION: PCR primer

<400> SEQUENCE: 35
cacctgcgtc accggggaat tccgatctag taacatagat g 41

<210> SEQ ID NO 36
<211> LENGTH: 70
<212> TYPE: DNA
<213> ORGANISM: Artificial Sequence
<220> FEATURE:
<223> OTHER INFORMATION: PCR primer

<400> SEQUENCE: 36
taatacgact cactatatcc ggatcaaaag caggtgatgt tctttcctgc gttatcccct 60
gattctgtgg 70

<210> SEQ ID NO 37
<211> LENGTH: 49
<212> TYPE: DNA
<213> ORGANISM: Artificial Sequence
<220> FEATURE:
<223> OTHER INFORMATION: PCR primer

<400> SEQUENCE: 37
ctcctcgccc ttgctcacca tggtataagc tgtttcctgt gtgaaattg 49

<210> SEQ ID NO 38
<211> LENGTH: 37
<212> TYPE: DNA
<213> ORGANISM: Artificial Sequence
<220> FEATURE:
<223> OTHER INFORMATION: PCR primer

<400> SEQUENCE: 38
ggaaacagct tataccatgg tgagcaaggg cgaggag 37

<210> SEQ ID NO 39
<211> LENGTH: 56
<212> TYPE: DNA
<213> ORGANISM: Artificial Sequence
<220> FEATURE:
<223> OTHER INFORMATION: PCR primer

<400> SEQUENCE: 39
ggaacaaaag ctggagctcc ggtgacgcag gtgttacttg tacagctcgt ccatgc 56

<210> SEQ ID NO 40
<211> LENGTH: 21
<212> TYPE: DNA
<213> ORGANISM: Artificial Sequence
<220> FEATURE:
<223> OTHER INFORMATION: PCR primer

<400> SEQUENCE: 40
cacacggtgc caatttatga a 21

<210> SEQ ID NO 41
<211> LENGTH: 18
<212> TYPE: DNA
<213> ORGANISM: Artificial Sequence
<220> FEATURE:
<223> OTHER INFORMATION: PCR primer

<400> SEQUENCE: 41
gatcacggcc agcaaggt 18

<210> SEQ ID NO 42
<211> LENGTH: 20
<212> TYPE: DNA
<213> ORGANISM: Artificial Sequence
<220> FEATURE:
<223> OTHER INFORMATION: PCR primer

<400> SEQUENCE: 42
aaggcacaag cctatcctgc 20

<210> SEQ ID NO 43
<211> LENGTH: 20
<212> TYPE: DNA
<213> ORGANISM: Artificial Sequence
<220> FEATURE:
<223> OTHER INFORMATION: PCR primer

<400> SEQUENCE: 43
tggtcattcg gtgccagttt 20

<210> SEQ ID NO 44
<211> LENGTH: 24
<212> TYPE: DNA
<213> ORGANISM: Artificial Sequence
<220> FEATURE:
<223> OTHER INFORMATION: PCR primer

<400> SEQUENCE: 44
tggagatata aagacgcgaa aaac 24

<210> SEQ ID NO 45
<211> LENGTH: 19
<212> TYPE: DNA
<213> ORGANISM: Artificial Sequence
<220> FEATURE:
<223> OTHER INFORMATION: PCR primer

<400> SEQUENCE: 45
ggcatccagg agggactca 19

<210> SEQ ID NO 46
<211> LENGTH: 22
<212> TYPE: DNA
<213> ORGANISM: Artificial Sequence
<220> FEATURE:
<223> OTHER INFORMATION: PCR primer

<400> SEQUENCE: 46
ctggcatggc ctctatggta ct 22

<210> SEQ ID NO 47
<211> LENGTH: 22
<212> TYPE: DNA
<213> ORGANISM: Artificial Sequence
<220> FEATURE:
<223> OTHER INFORMATION: PCR primer

<400> SEQUENCE: 47
tgtcctggat ggtgcttcaa ct 22

<210> SEQ ID NO 48
<211> LENGTH: 19
<212> TYPE: DNA
<213> ORGANISM: Artificial Sequence
<220> FEATURE:
<223> OTHER INFORMATION: PCR primer

<400> SEQUENCE: 48
gtggaggcca acggaaatg 19

<210> SEQ ID NO 49
<211> LENGTH: 21
<212> TYPE: DNA
<213> ORGANISM: Artificial Sequence
<220> FEATURE:
<223> OTHER INFORMATION: PCR primer

<400> SEQUENCE: 49
cgtccgattg tgataccgag a 21

<210> SEQ ID NO 50
<211> LENGTH: 21
<212> TYPE: DNA
<213> ORGANISM: Artificial Sequence
<220> FEATURE:
<223> OTHER INFORMATION: PCR primer

<400> SEQUENCE: 50
aaacacctgc cgttacactc g 21

<210> SEQ ID NO 51
<211> LENGTH: 23
<212> TYPE: DNA
<213> ORGANISM: Artificial Sequence
<220> FEATURE:
<223> OTHER INFORMATION: PCR primer

<400> SEQUENCE: 51
cggaagcaag atcatcatcg tat 23

<210> SEQ ID NO 52
<211> LENGTH: 23
<212> TYPE: DNA
<213> ORGANISM: Artificial Sequence
<220> FEATURE:
<223> OTHER INFORMATION: PCR primer

<400> SEQUENCE: 52
ttccaccttc tcaaagatgt tcc 23

<210> SEQ ID NO 53
<211> LENGTH: 24
<212> TYPE: DNA
<213> ORGANISM: Artificial Sequence
<220> FEATURE:
<223> OTHER INFORMATION: PCR primer

<400> SEQUENCE: 53
gctcaactct gtttcaactt ggtc 24

<210> SEQ ID NO 54
<211> LENGTH: 19
<212> TYPE: DNA
<213> ORGANISM: Artificial Sequence
<220> FEATURE:
<223> OTHER INFORMATION: PCR primer

<400> SEQUENCE: 54
tcctgccacg gtcaaacct 19

<210> SEQ ID NO 55
<211> LENGTH: 19
<212> TYPE: DNA
<213> ORGANISM: Artificial Sequence
<220> FEATURE:
<223> OTHER INFORMATION: PCR primer

<400> SEQUENCE: 55
aagagcgagc gacggaatc 19

<210> SEQ ID NO 56
<211> LENGTH: 25
<212> TYPE: DNA
<213> ORGANISM: Artificial Sequence
<220> FEATURE:
<223> OTHER INFORMATION: PCR primer

<400> SEQUENCE: 56
gagtacagtg agaagctgat gggtc 25

<210> SEQ ID NO 57

<211> LENGTH: 21
<212> TYPE: DNA
<213> ORGANISM: Artificial Sequence
<220> FEATURE:
<223> OTHER INFORMATION: PCR primer

<400> SEQUENCE: 57
ggttgagggc acttgggata g 21

<210> SEQ ID NO 58
<211> LENGTH: 21
<212> TYPE: DNA
<213> ORGANISM: Artificial Sequence
<220> FEATURE:
<223> OTHER INFORMATION: PCR primer

<400> SEQUENCE: 58
ttgaggatgg tgaaggtggg a 21

<210> SEQ ID NO 59
<211> LENGTH: 19
<212> TYPE: DNA
<213> ORGANISM: Artificial Sequence
<220> FEATURE:
<223> OTHER INFORMATION: PCR primer

<400> SEQUENCE: 59
cttttgggcg acgcagaac 19

<210> SEQ ID NO 60
<211> LENGTH: 23
<212> TYPE: DNA
<213> ORGANISM: Artificial Sequence
<220> FEATURE:
<223> OTHER INFORMATION: PCR primer

<400> SEQUENCE: 60
gttatcaagc ctaccgtaca ggg 23

<210> SEQ ID NO 61
<211> LENGTH: 24
<212> TYPE: DNA
<213> ORGANISM: Artificial Sequence
<220> FEATURE:
<223> OTHER INFORMATION: PCR primer

<400> SEQUENCE: 61
agttccagca gacgaagtgt aaat 24

<210> SEQ ID NO 62
<211> LENGTH: 22
<212> TYPE: DNA
<213> ORGANISM: Artificial Sequence
<220> FEATURE:
<223> OTHER INFORMATION: PCR primer

<400> SEQUENCE: 62
aggtgcccac agtcgacata gc 22

<210> SEQ ID NO 63
<211> LENGTH: 20
<212> TYPE: DNA
<213> ORGANISM: Artificial Sequence
<220> FEATURE:
<223> OTHER INFORMATION: PCR primer

<400> SEQUENCE: 63
cgcctgtcca gccactctaa 20

<210> SEQ ID NO 64
<211> LENGTH: 23
<212> TYPE: DNA
<213> ORGANISM: Artificial Sequence
<220> FEATURE:
<223> OTHER INFORMATION: PCR primer

<400> SEQUENCE: 64
attcgaggaa ctagaccctg acc 23

<210> SEQ ID NO 65
<211> LENGTH: 24
<212> TYPE: DNA
<213> ORGANISM: Artificial Sequence
<220> FEATURE:
<223> OTHER INFORMATION: PCR primer

<400> SEQUENCE: 65
gccacagact taggattacg cttg 24

<210> SEQ ID NO 66
<211> LENGTH: 28
<212> TYPE: DNA
<213> ORGANISM: Artificial Sequence
<220> FEATURE:
<223> OTHER INFORMATION: PCR primer

<400> SEQUENCE: 66
ttgatccccc tcgagatccg tcaacatg 28

<210> SEQ ID NO 67
<211> LENGTH: 32
<212> TYPE: DNA
<213> ORGANISM: Artificial Sequence
<220> FEATURE:
<223> OTHER INFORMATION: PCR primer

<400> SEQUENCE: 67
caattctttt ccatggtcgt cctctccaaa tg 32

<210> SEQ ID NO 68
<211> LENGTH: 34
<212> TYPE: DNA
<213> ORGANISM: Artificial Sequence
<220> FEATURE:
<223> OTHER INFORMATION: PCR primer

<400> SEQUENCE: 68
gaggacgacc atggaaaaga attgtcgtgg agtg 34

<210> SEQ ID NO 69
<211> LENGTH: 38
<212> TYPE: DNA
<213> ORGANISM: Artificial Sequence
<220> FEATURE:
<223> OTHER INFORMATION: PCR primer

<400> SEQUENCE: 69
gggaaattca agcttttaat ttccaatttg ttgggcct 38

<210> SEQ ID NO 70
<211> LENGTH: 34
<212> TYPE: DNA

<213> ORGANISM: Artificial Sequence
<220> FEATURE:
<223> OTHER INFORMATION: PCR primer

<400> SEQUENCE: 70
tggaaattaa aagcttgaat ttccccgatc gttc 34

<210> SEQ ID NO 71
<211> LENGTH: 33
<212> TYPE: DNA
<213> ORGANISM: Artificial Sequence
<220> FEATURE:
<223> OTHER INFORMATION: PCR primer

<400> SEQUENCE: 71
ggctgcagga attccgatct agtaacatag atg 33

<210> SEQ ID NO 72
<211> LENGTH: 32
<212> TYPE: DNA
<213> ORGANISM: Artificial Sequence
<220> FEATURE:
<223> OTHER INFORMATION: PCR primer

<400> SEQUENCE: 72
aagcttgata tcgaattcga tccgtcaaca tg 32

<210> SEQ ID NO 73
<211> LENGTH: 37
<212> TYPE: DNA
<213> ORGANISM: Artificial Sequence
<220> FEATURE:
<223> OTHER INFORMATION: PCR primer

<400> SEQUENCE: 73
ttggagagga cgaccatggc tactggtatc caaaacc 37

<210> SEQ ID NO 74
<211> LENGTH: 37
<212> TYPE: DNA
<213> ORGANISM: Artificial Sequence
<220> FEATURE:
<223> OTHER INFORMATION: PCR primer

<400> SEQUENCE: 74
ttggagagga cgaccatggc tactggtatc caaaacc 37

<210> SEQ ID NO 75
<211> LENGTH: 45
<212> TYPE: DNA
<213> ORGANISM: Artificial Sequence
<220> FEATURE:
<223> OTHER INFORMATION: PCR primer

<400> SEQUENCE: 75
gggaaattct ctagatcaag acttcataat aactttctga agagc 45

<210> SEQ ID NO 76
<211> LENGTH: 42
<212> TYPE: DNA
<213> ORGANISM: Artificial Sequence
<220> FEATURE:
<223> OTHER INFORMATION: PCR primer

<400> SEQUENCE: 76
gttattatga agtcttgatc tagagaattt ccccgatcgt tc 42

<210> SEQ ID NO 77
<211> LENGTH: 38
<212> TYPE: DNA
<213> ORGANISM: Artificial Sequence
<220> FEATURE:
<223> OTHER INFORMATION: PCR primer

<400> SEQUENCE: 77
gaacaaaagc tggagctccc gatctagtaa catagatg 38

<210> SEQ ID NO 78
<211> LENGTH: 33
<212> TYPE: DNA
<213> ORGANISM: Artificial Sequence
<220> FEATURE:
<223> OTHER INFORMATION: PCR primer

<400> SEQUENCE: 78
ctagatcgga attcctgcag gatccgtcaa cat 33

<210> SEQ ID NO 79
<211> LENGTH: 32
<212> TYPE: DNA
<213> ORGANISM: Artificial Sequence
<220> FEATURE:
<223> OTHER INFORMATION: PCR primer

<400> SEQUENCE: 79
gatcccccgg gctgcaggaa ttccgatcta gt 32

ANTHOCYANIN BIOSYNTHESIS IN CARROT PLANTS

The present invention relates to transgenic carrot plants comprising at least one heterologous DNA sequence encoding a transcription factor gene or a transcription factor gene operably linked to a promoter, which is expressed in the transgenic plant and increases the expression of at least one gene encoding a sinapic acid glucosyltransferase (USAGT). The USAGT can have the sequence of SEQ ID NO:4 or a sequence having at least 85% identity to SEQ ID NO:4. The invention further relates to DNA sequences encoding transcription factor genes DcMYB90 (SEQ ID NO:1) and DcEGL1 (SEQ ID NO:2) as well as transgenic carrot plants comprising respective DNA sequences which may be operably linked to a heterologous promoter. The transgenic plants of the present invention can be used in methods of preparing a composition comprising anthocyanins, which methods may comprise steps of producing a transgenic carrot plant of the invention and isolating the composition comprising anthocyanins from the taproot of the carrot plants. In preferred embodiments the composition comprises cyanidin 3-xylosyl(sinapoylglucosyl)galactoside in a concentration of at least 30% of the total anthocyanin concentration.

TECHNICAL BACKGROUND

Anthocyanins are water-soluble natural pigments, which belong to a highly diverse group of specialized secondary metabolites, known as flavonoids. Apart from their essential role in protection against UV-B and against various biotic and abiotic stress factors, they also impart vibrant colors to various plant organs, i.e. fruits, flowers and tubers. The color of anthocyanins ranges from orange-red to blue-purple depending on their structural modifications, i.e. glycosylation, methylation or acylation, as well as physiological conditions such as pH, metal ion chelation and co-pigmentation. The availability of anthocyanins in a wide range of colors has resulted in an increased interest in anthocyanins from the natural food color industry. While adverse effects of hydrocarbon based synthetic colors on humans have been reported, anthocyanins are known to have antioxidant properties in vitro and are approved for use as food colorants in the European Union and other states. As a result, there is an increasing demand for natural colors and in particular anthocyanins in the food industry.

Black carrots (*Daucus carota* subsp. *sativus* var. *atrorubens*) represent a potential source of anthocyanin production. Black (purple) carrots naturally produce cyanidin-based glycosylated anthocyanins with a high percentage of acylated anthocyanins. A high content of acylated anthocyanins is advantageous for the intended use as food colors because acylated anthocyanins are more stable than non-acylated anthocyanins. However, the total amount of anthocyanins in black carrots is too low to use these plants as a commercially viable source of anthocyanin production.

The predominant anthocyanins in the taproots of black carrots are derived from cyanidin. Recent studies in black carrots have identified structural genes associated with cyanidin synthesis. These include the PAL3, C4H1, 4CL1 genes of the general phenylpropanoid pathway providing the flux for the anthocyanin pathway, the CHS1, CHI1, F3H1, F3'H1, DFR1 and LDOX1 genes leading to cyanidin synthesis, and the DcUCGalT1 gene responsible for the further glycosylation of cyanidin, respectively (FIG. 6). The regulatory genes which control transcription of the structural genes of the anthocyanin pathway in carrots are unknown.

Accordingly, there is a need for improved methods of producing stable anthocyanin compositions suitable for use in the food color industry.

SUMMARY OF THE INVENTION

The present invention solves this problem by providing transgenic carrot plants comprising at least one heterologous DNA sequence encoding a transcription factor gene operably linked to a promoter, wherein the transcription factor is expressed in the transgenic plant and increases the expression of at least one gene encoding a sinapic acid glucosyltransferase (USAGT). The increase of the expression of at least one USAGT encoding gene is obtained in relation to an orange carrot plant not comprising the heterologous DNA sequence.

The USAGT gene can have the sequence of SEQ ID NO:4 or a sequence having at least 85% identity to SEQ ID NO:4, while maintaining the sinapic acid glucosyltransferase activity of the protein of SEQ ID NO:4. The present invention also provides transgenic carrot plants, wherein the plant comprises two heterologous DNA sequences each encoding a transcription factor gene. The DNA sequence encoding a transcription factor gene is preferably the DNA sequence of DcMYB90 (SEQ ID NO:1) and/or the DNA sequence of DcEGL1 (SEQ ID NO:2).

In a further embodiment the present invention the expression of the one or two transcription factors in the transgenic carrot plants of the present invention increases the expression of at least one gene selected from the following group are CHS1, CHI1, F3H1, F3'H1, DFR1, LDOX1 and UCGalT1.

The invention also provides parts of these plants, including taproots, carrot tissues and carrot cells, for example in suspension cell culture. The transgenic carrot plants of the present invention are transgenic *Daucus carota* subsp. *sativus* plants. The plants are preferably not black carrot plants, i.e. not *Daucus carota* subsp. *sativus* var. *atrorubens* plants. In a further preferred embodiment, the plants used for transformation are orange carrot plants.

The present inventors surprisingly found that increasing the expression of at least one gene encoding a sinapic acid glucosyltransferase (USAGT) in a transgenic carrot plant leads to significant increases in the concentration of cyanidin 3-xylosyl(sinapoylglucosyl)galactoside in the taproot of the transgenic carrot plant, which represents a stable and highly advantageous anthocyanin.

In a further embodiment the present invention provides DNA sequences encoding a transcription factor gene selected from the list comprising DcMYB90 (SEQ ID NO:1) and DcEGL1 (SEQ ID NO:2), wherein the transcription factor gene is operably linked to a heterologous promoter and wherein the heterologous promoter achieves an increase in the expression in comparison to the expression of the corresponding transcription factor linked to its natural promoter of more than 30%. Alternatively, the DNA sequences of the present invention may comprise a sequence having at least 80% identity to the sequence of SEQ ID NO:1 or SEQ ID NO:2, wherein the sequence encodes a transcription factor protein capable of increasing the expression of sinapic acid glucosyltransferase (USAGT) having the sequence of SEQ ID NO:4. Again, the transcription factor gene is operably linked to a heterologous promoter and the heterologous promoter achieves an increase in the expression in comparison to the expression of the corresponding transcription factor linked to its natural promoter of more than 30%.

In certain embodiments, the DNA sequences of the present invention can be the CaMV 35 S promoter comprising the sequence of SEQ ID NO:3 or a sequence having at least 80% identity to the sequence of SEQ ID NO:3, which sequence achieves an expression of a coding sequence in a plant cell of at least 80% of the sequence of SEQ ID NO:3.

In a further aspect the present invention provides methods of producing the carrot plants of the present invention which methods comprise transforming an orange carrot plant with a DNA sequence encoding:

(a) a promoter of a transcription factor gene; or (b) a transcription factor gene operably linked to a promoter;

wherein the heterologous DNA sequence increases the expression of at least one gene encoding a sinapic acid glucosyltransferase (USAGT).

These methods may make use of a DNA sequence encoding the transcription factor gene DcMYB90 linked to a heterologous promoter and/or a DNA sequence encoding the transcription factor gene DcEGL1 linked to a heterologous promoter. Again, the heterologous promoter may be any highly active heterologous promoter and preferably is:

(a) the CaMV 35 S promoter comprising the sequence of SEQ ID NO:3; or (b) a sequence having at least 80% identity to the sequence of SEQ ID NO:3, which sequence achieves an expression of a coding sequence in a plant cell of at least 80% of the sequence of SEQ ID NO:3.

In a different embodiment the present invention provides methods of preparing a composition comprising anthocyanins, comprising a method of producing a carrot plant as described above and isolating the composition comprising anthocyanins from the taproot of the carrot plants, wherein the composition comprises cyanidin 3-xylosyl(sinapoylglucosyl)galactoside in a concentration of at least 30% of the total anthocyanin concentration.

Accordingly, the invention also provides compositions comprising anthocyanins, wherein the relative concentration of cyanidin 3-xylosyl(sinapoylglucosyl)galactoside is at least 30% of the total anthocyanin concentration. These compositions are preferably obtained by the above methods. In one aspect the compositions are further characterized in a relative concentration of cyanidin 3-xylosylgalactoside which is less than 30% of the total anthocyanin concentration.

In a further aspect, methods of producing or coloring a food product are provided, which comprise adding a composition comprising anthocyanins to a food product precursor, wherein the composition comprising anthocyanins is obtainable by a method or a composition as described above.

The following abbreviations are used throughout the application:

CHI: chalcone isomerase;

CHS: Chalcone synthase;

C3xg: Cyanidin 3-xylosylgalactoside;

C3x(G)g: Cyanidin 3-xylosyl(glucosyl)galactoside;

C3x(CG)g: Cyanidin 3-xylosyl(coumaroylglucosyl)galactoside;

C3x(FG)g: Cyanidin 3-xylosyl(feruloylglucosyl)galactoside;

C3x(SG)g: Cyanidin 3-xylosyl(sinapoylglucosyl)galactoside;

C4H: cinnamate 4-hydroxylase;

DFR: dihydroflavonol 4-reductase;

FLS: flavanol synthase;

F3H: flavanone 3-hydroxylase;

F3'H: flavonoid-3'-hydroxylase;

F3'5'H: flavonoid-3'-5'-hydroxylase;

LAR: leucoanthocyanidin reductase; ANR, anthocyanidin reductase;

LDOX/ANS: leucoanthocyanidin dioxygenase/anthocyanidin synthase;

PAL: phenylalanine ammonia lyase;

P3x(SG)g: Peonidin 3-xylosyl(sinapoylglucosyl)galactoside;

3AT: acyl transferase;

3GT: 3'-glucosyl transferase; OMT, 0-methyl transferase;

4CL: 4-coumarate: coenzyme A ligase.

BRIEF DESCRIPTION OF THE FIGURES

FIG. 1 shows primers used for PCR and cloning of the open reading frames (ORF)s of carrot transcription factors (TFs) involved in anthocyanin biosynthesis.

FIG. 2 shows the sequences of overlapping infusion primers used for creating Entry vectors for DcMYB90, DcEGL1 and cloning BFP into Destination vector for selection.

FIG. 3 shows the sequences of RT-qPCR primers used for estimation of expression levels of transgenes and biosynthetic genes in L1 and L2.

FIG. 4 shows the relative abundance of anthocyanins based on peak area in HPLC chromatograms; TMA: Total monomeric anthocyanin content, expressed in cyanidin-3-O-glucoside equivalents in mg $g^{-1}$.

FIG. 5 shows the relative abundance of anthocyanins based on peak area of their LC-MS/MS profiles; TSA: Total soluble anthocyanin content, expressed in mg $g^{-1}$; Standard deviation among 3 replicates are reported in table as ±; C3xg: Cyanidin 3-xylosylgalactoside was detected in trace amounts.

FIG. 7 shows the structure of anthocyanins after Petroni, K. & Tonelli, C. Recent advances on the regulation of anthocyanin synthesis in reproductive organs. Plant Sci. 181, 219-229 (2011).

FIG. 8 shows a schematic overview of steps involved in pTE90-E1 transformation vector construction.

a) & b) 6 weeks after culture initiation, a: Non-transformed control callus, b: Callus induced on pTM90-E1 infected explants;

c) & d) Regenerated plantlets two months after transfer to regeneration medium, c: Plantlet from an explant infected with the pTM90-E1 vector, d: Plantlet from a non-infected explant;

e) & f) Leaves from mature plants three months after transfer to the greenhouse, e: Mature non-transformed plant, f: Mature pTM90-E1 transformed plant;

g)-i) Taproots from mature plants three months after transfer to the greenhouse, g: Taproot from a non-transformed control plant, h) and i): Taproot from a pTM90-E1 transformed plant, Black bar indicates 1 cm.

Figure 10:
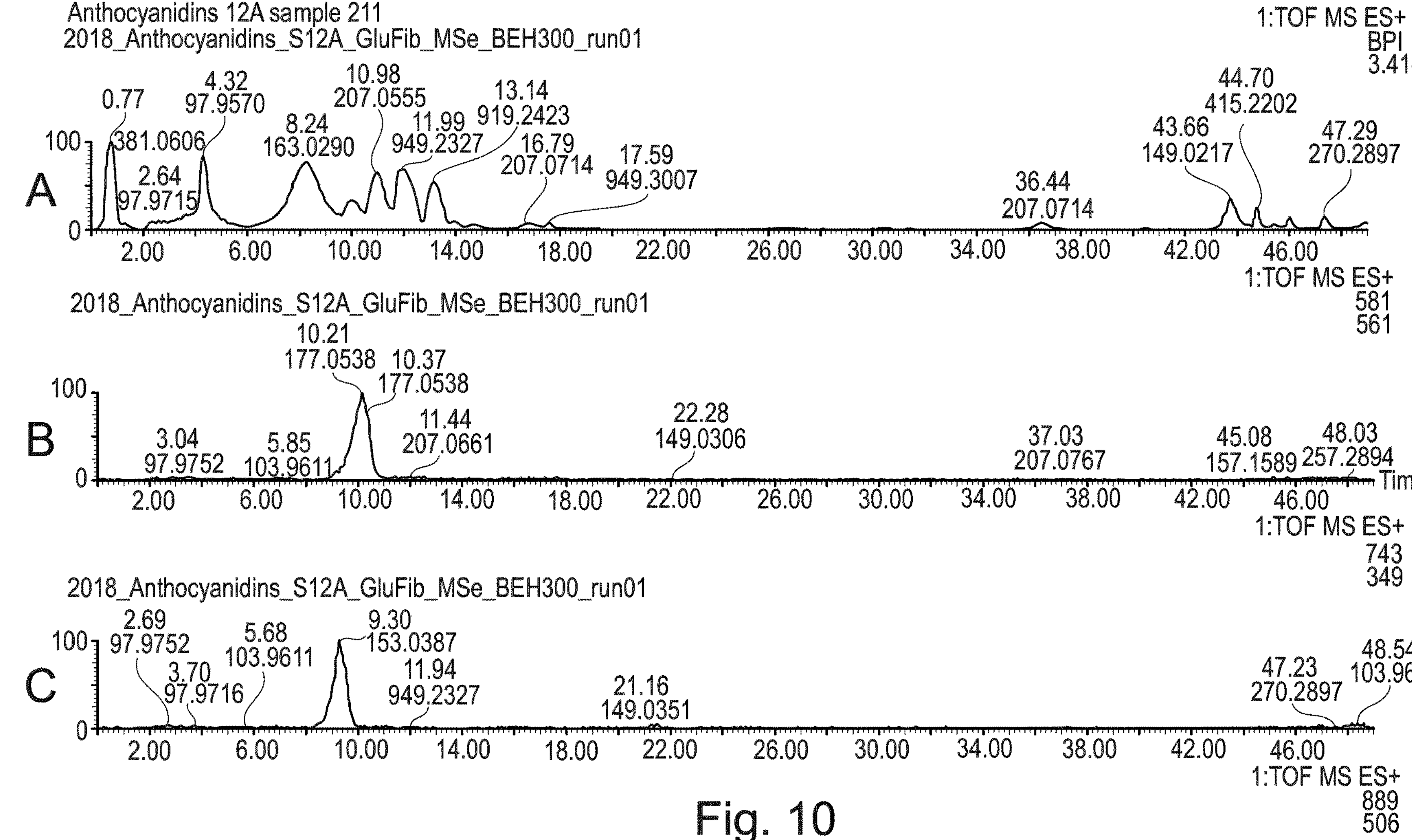
Figure 10:
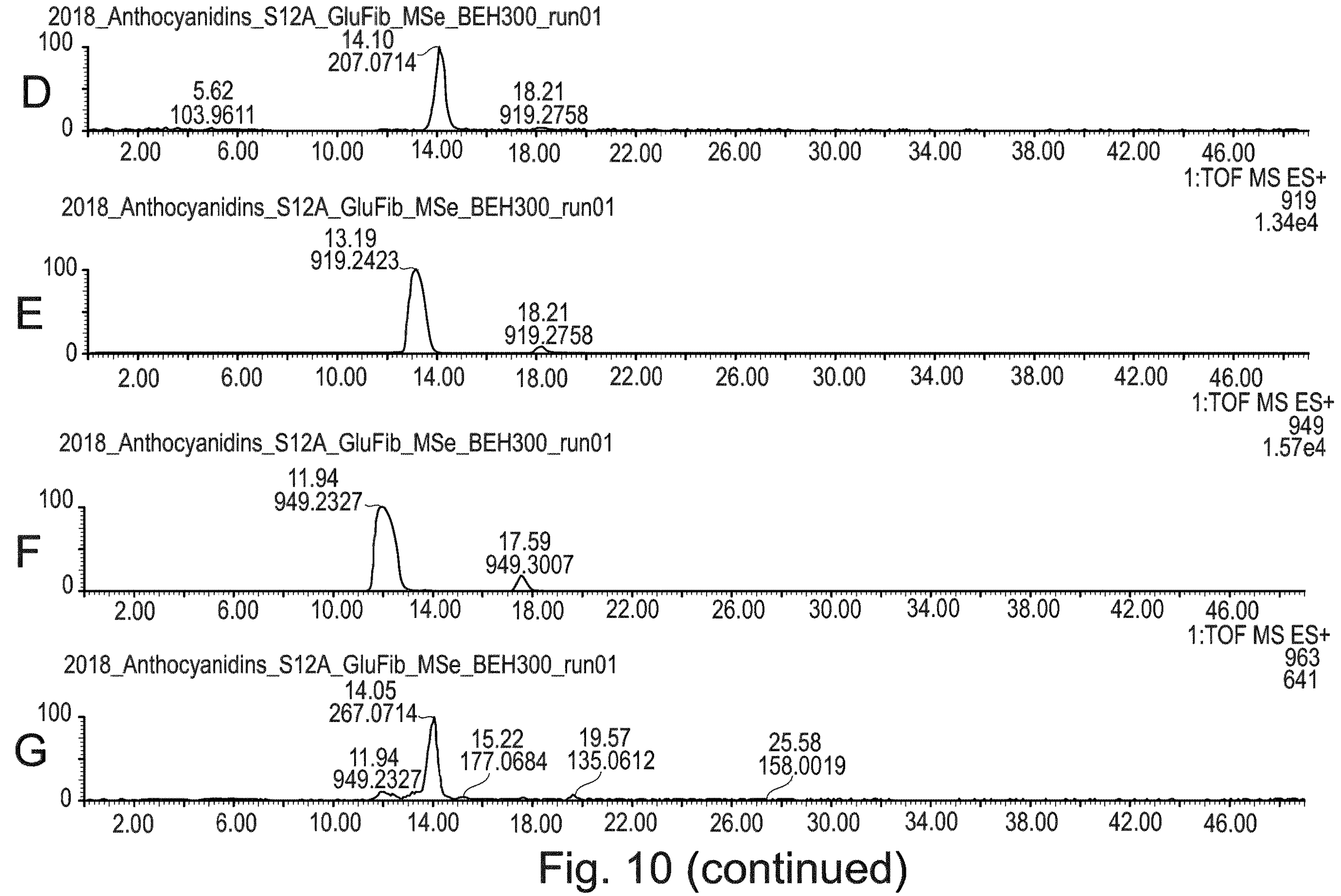

FIG. 10 shows the anthocyanins detected by LC-MS, which comprises the MS survey scan of Line L1 (trace A) and extracted ion chromatograms of selected m/z species: 433 (Panel B), 743: C3x(G)g (Panel C), 919: C3x(FG)g (Panel D), 949: C3x(SG)g (Panel E), 963: P3x(SG)g (Panel F) and 1111 (Panel G).

Figure 6:
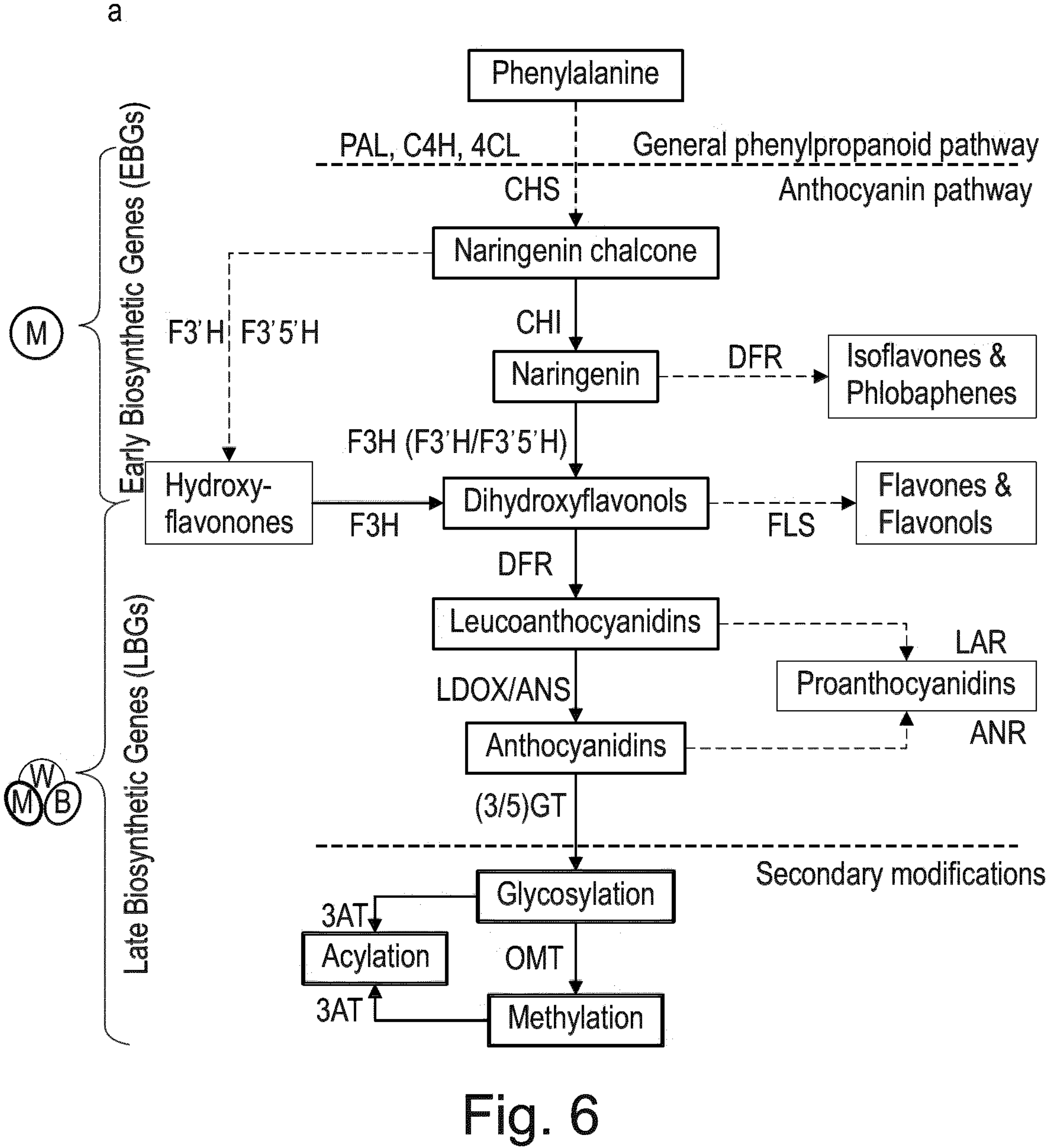
FIG. 6 provides a schematic diagram of the flavonoid pathway, comprising of general phenylpropanoid pathway, anthocyanin pathway leading to synthesis of anthocyanins and other subgroups. MYB (M), bHLH (B) and WD40 (W) transcription factors controlling anthocyanin pathway and putative MBW complexes are indicated. Structural enzymes are indicated in capital italic letters and intermediate compounds are represented in boxes. Anthocyanin pathway genes are indicated in Black, other branches of flavonoid pathway are indicated in Grey. Structural genes identified in Carrots are marked in Bold. Bold arrows indicate direct conversion, Dashed arrows indicates conversion through intermediates.
Figure 11:
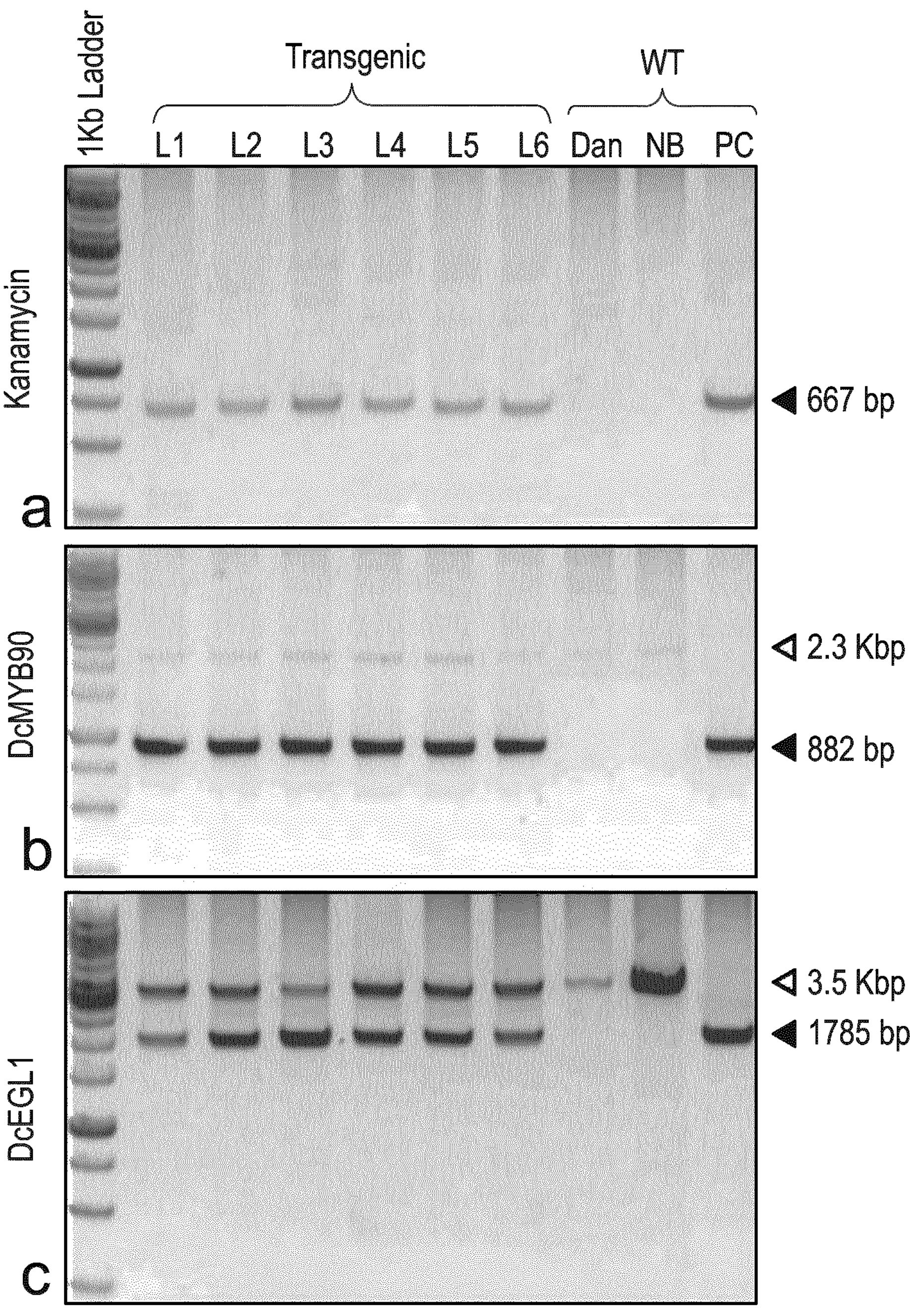

FIG. 11 shows the PCR confirmation of T-DNA integration in pTM90-E1 transformed plants: a) Amplification of 697 bp region of encompassing the nptII and CaMV terminator. b) Amplification of 882 bp region of DcMYB90 CDS and 2.3 Kbp region of genomic sequence. c) Amplification of 1.785 Kbp region of DcEGL1 CDS and 3.5 Kbp region of genomic sequence. CDS and genomic amplification products are represented with Dark and Light arrows respectively. L1-L6 represents 6 transgenic T0 plants. L1 and L2 had almost completely purple taproots, whereas L3 was almost completely orange. L3-L6 had variable levels of pigmented taproots. WT represents Wild type Danvers 126 plant (Dan) and Night Bird (NB). PC represents pTM90-E1 vector as positive control. Primer pair sequences are listed in FIG. 6. The plant names correspond to FIGS. 9 & 5.

Figure 12:
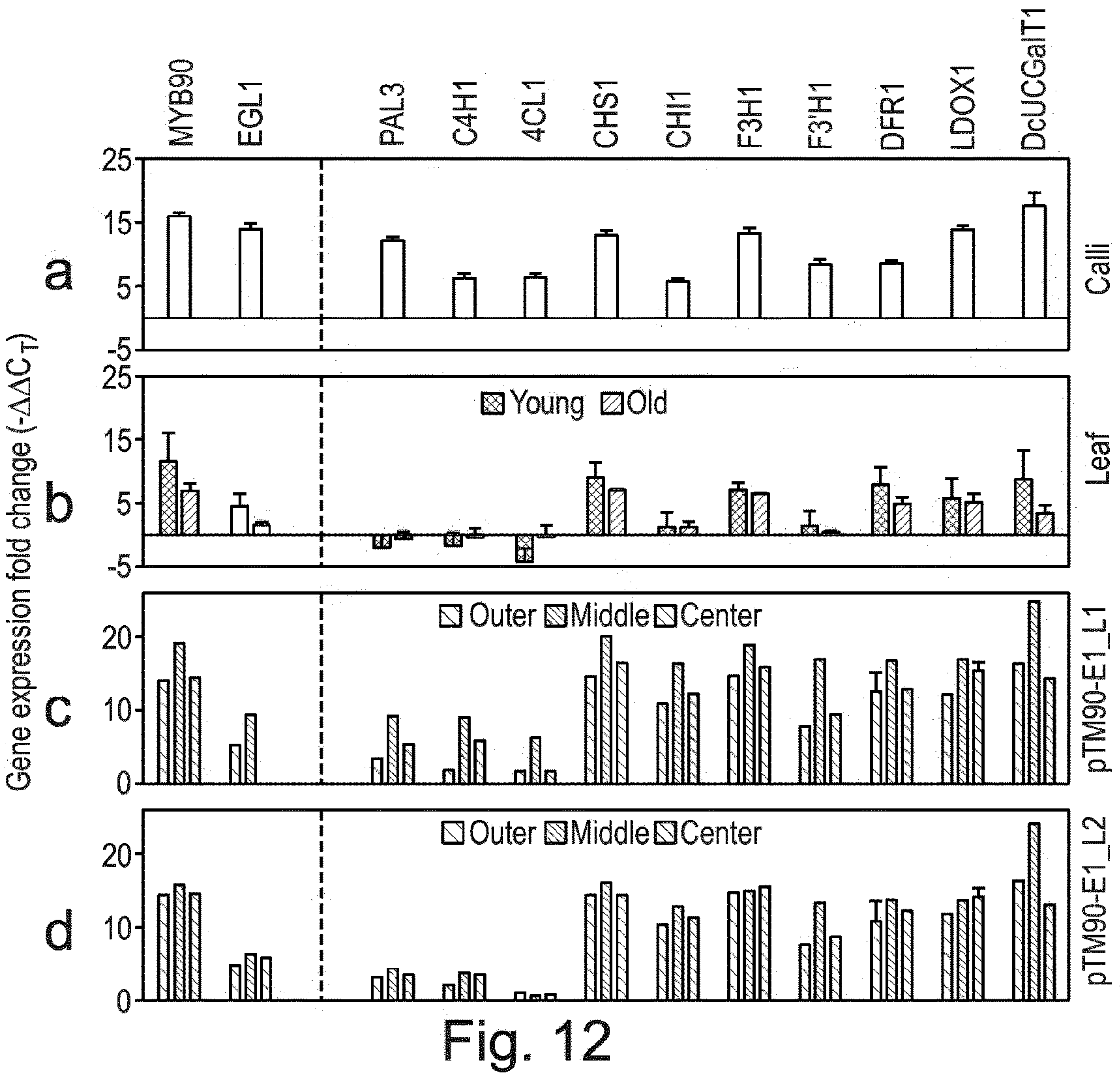

FIG. 12 shows the expression levels of DcMYB90, DcEGL1 and major biosynthetic genes in 3-month-old taproots of pTM90-E1 transformed plants. Plant names correspond to plant names in FIG. 5; pTM90_E1_L1, L2 are transgenic purple carrots.

FIG. 13 shows the list of infusion primers used to create pRos1, pDel and pRD transformation vectors. The promotor, CDS and terminator sequences for both pRos1 and pDel (single overexpression cassette vectors) were amplified using 3 PCR reactions using infusion primers, containing 8-15 bp overhang and unique restriction site (Bold and underlined) for modular editing and cloned into pBRACT102 destination vector linearized with respective restriction enzyme sets. The pRos1-Del dual overexpression vector was created by cloning overexpression cassette from pDel into pRos1 linearized with PstI.

FIG. 14 provides the composition of media used for Agrobacterium-mediated transformation of carrot hypocotyledons.

FIG. 15 illustrates the relative abundance of anthocyanins based on peak area in HPLC chromatograms; TMA: Total monomeric anthocyanin content, expressed in cyanidin-3-O-glucoside equivalents in mg $g^{-1}$.

FIG. 16 illustrates the relative abundance of anthocyanins based on peak area of their LC-MS/MS profiles; TSA: Total soluble anthocyanin content, expressed in mg $g^{-1}$. Visible threshold for detection was set to 3 mg $g^{-1}$, Standard deviation among 3 replicates are reported in table as ±.

FIG. 17 provides a schematic representation of AmRosea1 and AmDelila overexpression cassettes used in pRos1, pDel and pRD transformation vectors. All vectors contain left (LB) and right (RB) border sequences for stable integration. Kanamycin (nptII) controlled by the CaMV 35S promoter and NOS terminator was used as selection marker. Black triangles represents the restriction enzymes used for infusion cloning in respective vectors. pRos1 (A) and pDel (B) contains coding sequence of AmRosea1 and AmDelila controlled by CaMV 2×35S and the NOS terminator, respectively, whereas pRos-Del (C) contains coding sequences of both AmRosea1 and AmDelila individually controlled by the CaMV 2×35S and the NOS terminator.

FIG. 18 illustrates the development of carrots from callus to mature plants. a) Non-transformed control callus [6 weeks after culture initiation]; b) and c) Callus induced on pRD infected explants, b: Six weeks after culture initiation, c: Ten weeks after culture initiation; d) and e) Regenerated plantlets two months after transfer to regeneration medium, d: Plantlet from a non-infected explant, e: Plantlet from an explant infected with the pRD vector; f) and g) Mature plants three months after transfer to the greenhouse, f: Mature non-transformed plant, g: Mature pRD transformed plant; h)-l) Taproots from mature plants three months after transfer to the greenhouse, h and i: Taproot from a pRD transformed plant, j: Taproot from a non-transformed control plant, k: Taproot from a pRos1 trans-formed plant, l: Taproot from a pDel transformed plant. Black/White bar indicates 1 cm.

Figure 19:
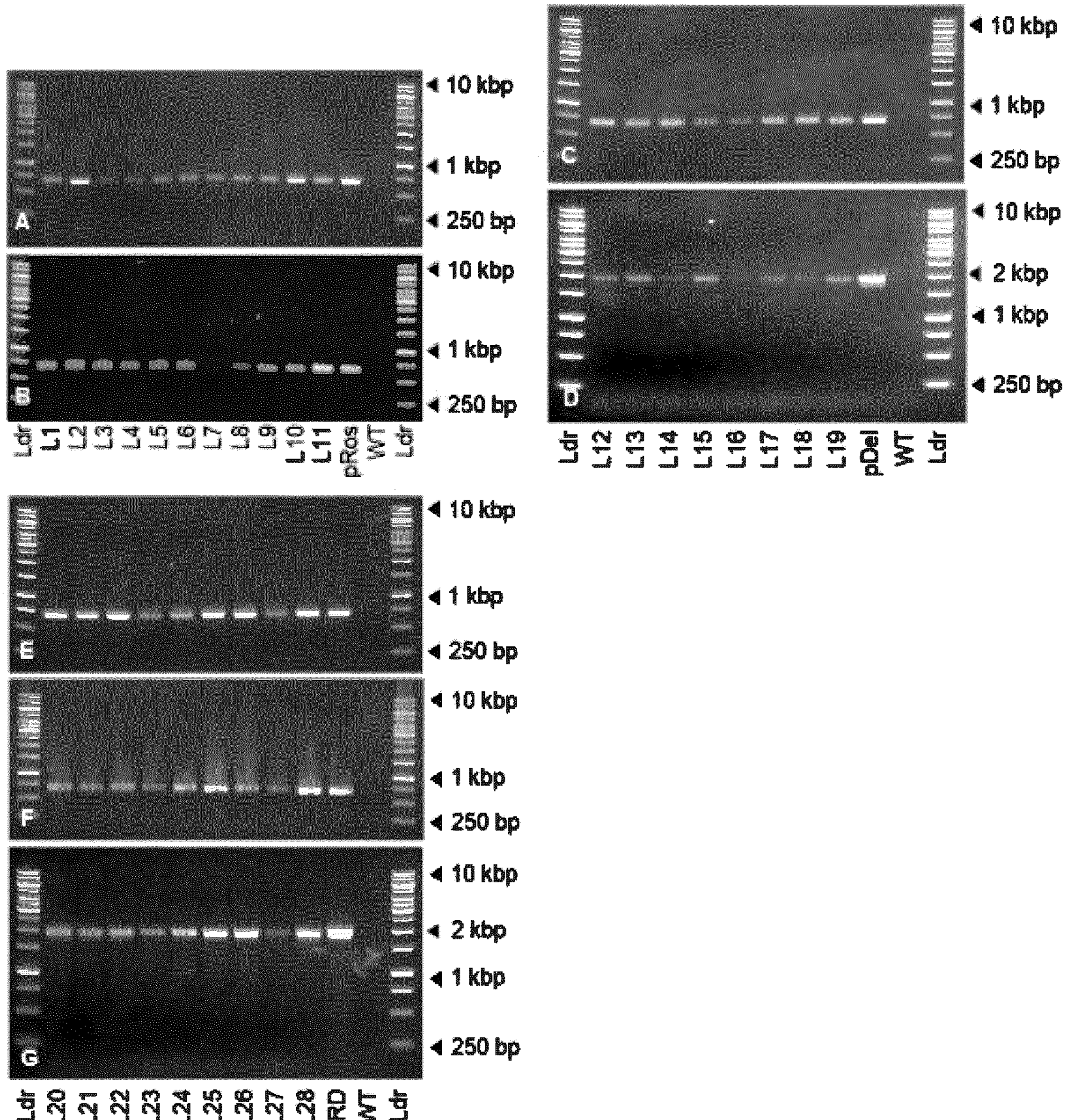

FIG. 19 shows PCR confirmation of T-DNA integration in pRos1, pDel and pRD transformed plants. A), C) and E) Amplification of 697 bp region of encompassing the nptII and CaMV terminator in pRos1. (A), pDel (C) and pRD (E) transformed plants, respectively. B) and F) Amplification of a 663 bp region of the AmRosea1 CDS in pRos1 and pRD transformed plants, respectively. D) and G) Amplification of 1935 bp region of the AmDelila CDS in pDel and pRD transformed plants, respectively. Ldr: GeneRuler 1Kbp ladder; pRos1, pDel, pRD vectors used as positive controls; WT: Non-transformed control; L1-11: pRos1 transformed plants; L12-19: pDel transformed plants; L20-28: pRD transformed plants.

Figure 20:
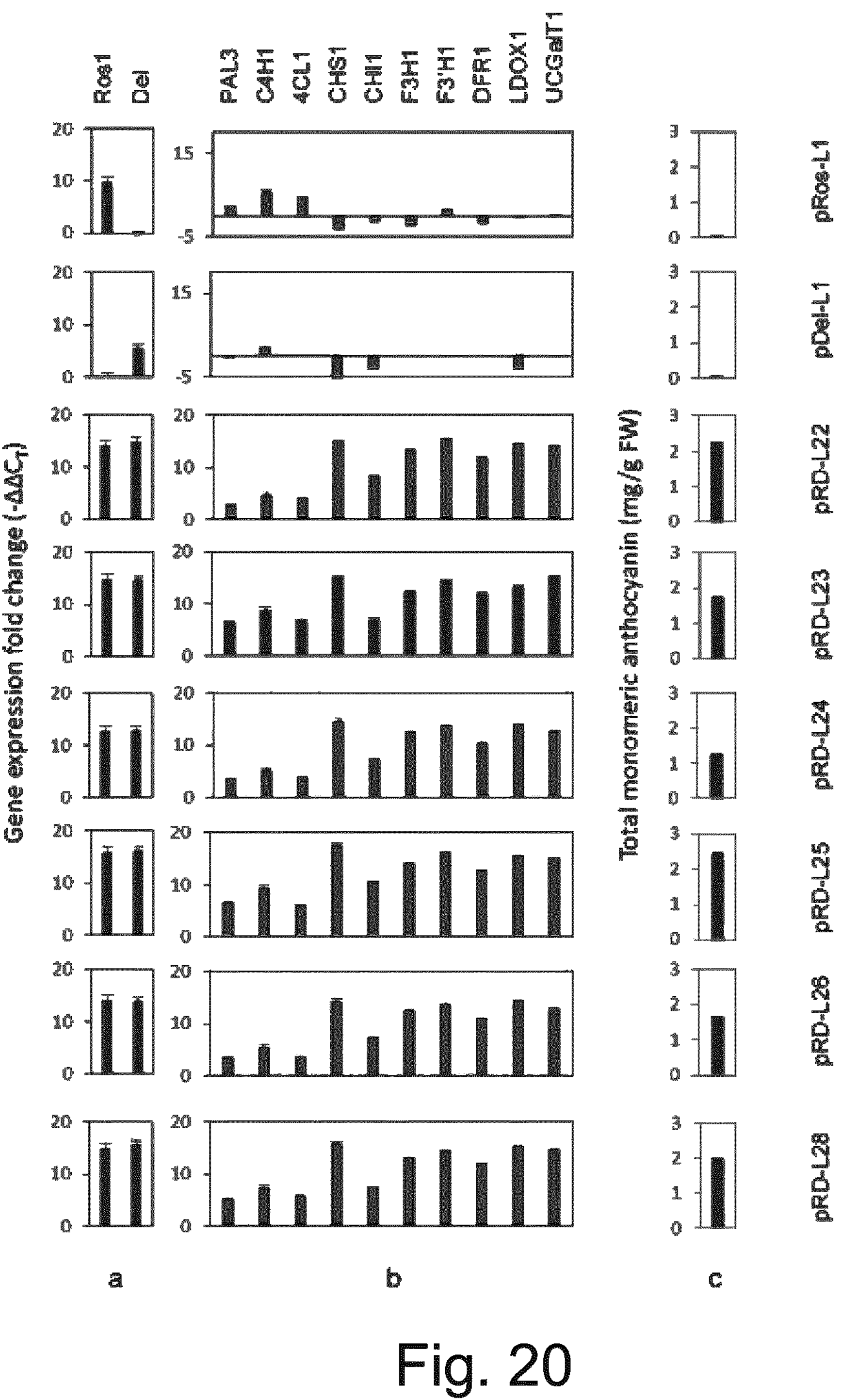

FIG. 20 shows the expression levels of AmRosea1, AmDelila and major biosynthetic genes and total monomeric anthocyanin content (mg $g^{-1}$ FW) in 3-month-old taproots of pRos, pDel and pRD transformed plants. a) Relative expression levels of the transgenes AmRosea1 and AmDelila. b) Expression levels of genes of the general phenylpropanoid pathway and the anthocyanin biosynthesis genes. c) Total monomeric anthocyanin content mg $g^{-1}$ FW.

BRIEF DESCRIPTION OF THE SEQUENCES

SEQ ID NO:1 coding sequence of DcMYB90;
SEQ ID NO:2 coding sequence of DcEGL1;
SEQ ID NO:3 sequence of CamV 35S promoter;
SEQ ID NO:4 coding sequence of USAGT;
SEQ ID NO:5 protein sequence of DcMYB90;
SEQ ID NO:6 protein sequence of DcEGL1;
SEQ ID NO:7 protein sequence of USAGT;
SEQ ID NOs:8-79 primer sequences.

DETAILED DESCRIPTION OF THE INVENTION

The present invention provides transgenic carrot plant comprising at least one heterologous DNA sequence encoding:

(a) a promoter of a transcription factor gene; or (b) a transcription factor gene operably linked to a promoter;

wherein the heterologous DNA sequence increases the expression of at least one gene encoding a sinapic acid glucosyltransferase (USAGT). The increase of the expression of at least one USAGT encoding gene is obtained in relation to an orange carrot plant not comprising the heterologous DNA sequence.

The USAGT gene sequence is a carrot USAGT gene sequence and can for example be the sequence of SEQ ID NO:4 or a sequence having at least 85% identity to SEQ ID NO:4 while maintaining the sinapic acid glucosyltransferase activity of the protein having SEQ ID NO:4.

The plants of the present invention may comprise one or two heterologous DNA sequences each encoding a transcription factor gene or a transcription factor gene operably linked to a promoter. In one embodiment the plants of the present invention comprise at least one heterologous DNA sequence encoding the transcription factor gene DcMYB90 (SEQ ID NO:1) and at least one DNA sequence encoding the transcription factor gene DcEGL1 (SEQ ID NO:2). Alternatively, the plants may encode a sequence having at least 80% identity to the sequence of SEQ ID NO:1 and at least 80% identity to the sequence of SEQ ID NO:2, wherein the sequence encodes a transcription factor protein increasing the expression of sinapic acid glucosyltransferase (USAGT) having the sequence of SEQ ID NO:4 in a transgenic plant comprising the heterologous DNA sequence in comparison to plants not comprising the heterologous sequence.

In a related embodiment the plants of the invention comprise two heterologous DNA sequences, one encoding the transcription factor gene DcMYB90 (SEQ ID NO:1) operably linked to a heterologous promoter and one encoding the transcription factor gene DcEGL1 (SEQ ID NO:2) operably linked to a heterologous promoter. Again, the plants may encode a sequence having at least 80% identity to the sequence of SEQ ID NO:1 and at least 80% identity to the sequence of SEQ ID NO:2, wherein the sequence encodes a transcription factor protein increasing the expression of sinapic acid glucosyltransferase (USAGT) having the sequence of SEQ ID NO:4 in a transgenic plant comprising the heterologous DNA sequence in comparison to plants not comprising the heterologous sequence. The heterologous promoter can be any recombinant heterologous promoter active in plants but preferably is the CamV 35 S promoter comprising the sequence of SEQ ID NO:3 or a sequence having at least 80% identity to the sequence of SEQ ID NO:3, which sequence achieves an expression of a coding sequence in a plant cell of at least 80% of the sequence of SEQ ID NO:3.

The expression of the one or more transcription factors may further increase the expression of one or more further genes, including at least one gene selected from the group consisting of CHS1, CHI1, F3H1, F3'H1, DFR1, LDOX1 and UCGalT1.

In a preferred embodiment the taproot of the transgenic carrot plants of the present invention comprise at least 30% C3x(SG)g of the total anthocyanin concentration.

The present invention further comprises part of the above transgenic carrot plants, wherein the part is a taproot, a carrot tissue or a carrot cell.

In a further embodiment the present invention provides DNA sequences encoding the heterologous DNA used for generating the transgenic plants of the invention described above. Respective DNA sequences may comprise a transcription factor gene selected from the list comprising DcMYB90 (SEQ ID NO:1) and DcEGL1 (SEQ ID NO:2) or a sequence having at least 80% identity to the sequence of SEQ ID NO:1 or SEQ ID NO:2, wherein the sequence encodes a transcription factor protein increasing the expression of sinapic acid glucosyltransferase (USAGT) having the sequence of SEQ ID NO:4. The transcription factor gene can be operably linked to a heterologous promoter and the heterologous promoter achieves an increase in the expression in comparison to the expression of the corresponding transcription factor linked to its natural promoter of more than 30%. In one embodiment the DNA sequence comprises the promoter sequence of the CaMV 35 S promoter comprising the sequence of SEQ ID NO:3 or a sequence having at least 80% identity to the sequence of SEQ ID NO:3, which sequence achieves an expression of a coding sequence in a plant cell of at least 80% of the sequence of SEQ ID NO:3.

In a further alternative the present invention provides methods of producing carrot plants comprising transforming an orange carrot plant with a heterologous DNA sequence encoding:

(a) a promoter of a transcription factor gene; or (b) a transcription factor gene operably linked to a promoter;

wherein the heterologous DNA sequence increases the expression of at least one gene encoding a sinapic acid glucosyltransferase (USAGT).

The DNA sequence encoding the transcription factor gene is preferably the sequence of DcMYB90 operably linked to a heterologous promoter and/or DcEGL1 is operably linked to a heterologous promoter.

The heterologous promoter can be the CaMV 35 S promoter comprising the sequence of SEQ ID NO:3 or a sequence having at least 80% identity to the sequence of SEQ ID NO:3, which sequence achieves an expression of a coding sequence in a plant cell of at least 80% of the sequence of SEQ ID NO:3 or the promoter of the transcription factor gene DcMYB90 having SEQ ID NO:1 and/or the promoter of the transcription factor gene DcEGL1 having SEQ ID NO:2.

The present invention further provides methods of preparing a composition comprising anthocyanins, comprising a method of producing a carrot plant of the present invention as described above and isolating the composition comprising anthocyanins from the taproot of the carrot plants of the present invention, wherein the composition comprises cyanidin 3-xylosyl(sinapoylglucosyl)galactoside in a concentration of at least 30% of the total anthocyanin concentration. The step of isolating anthocyanins from plants can be carried out according to known methods for isolating anthocyanins from plant tissue.

In a further aspect, the present invention provides new and useful compositions comprising anthocyanins, wherein the relative concentration of cyanidin 3-xylosyl(sinapoylglucosyl)galactoside is at least 30% of the total anthocyanin concentration. The compositions comprising anthocyanins can be isolated from the carrot plants of the present invention using the methods described above. The composition preferably contain a relative concentration of cyanidin 3-xylosylgalactoside of less than 30% of the total anthocyanin concentration.

The compositions comprising anthocyanins of the present invention are particularly suitable in methods of producing a food product, which methods comprise adding a composition comprising anthocyanins of the present invention to a food product precursor.

In a related aspect the compositions comprising anthocyanins of the present invention are used in methods of coloring a food product, which methods comprise steps of adding a composition comprising anthocyanins to a food product precursor.

The present invention amongst other provides a R2R3-MYB and a bHLH transcription factor from black carrot cv. 'Night Bird', which are named DcMYB90 and DcEGL1, respectively. The nucleotide sequences of these DNA molecules are provided as SEQ ID NOs: 1-2. The present invention is also based on the surprising finding that expression of a transcription factor under the control of a constitutive promoter can achieve up-regulation of biosynthetic genes and accumulation of cyanidin based anthocyanins across leaves, stems and taproots of orange carrots. The present invention further provides methods of producing said transgenic carrot plant. The anthocyanin composition of the plants of the present invention is significantly different from the black carrot cv. 'night bird'. The most abundant anthocyanin in the transgenic plants of the invention is cyanidin 3-xylosyl(sinapoylglucosyl)galactoside (C3x(SG)g), which exhibits a lower visual detection threshold and a higher pH stability than other cyaniding-based anthocyanins, such as cyanidin 3-xylosyl(feruloylglucosyl)galactoside (C3x(FG)g) and cyanidin 3-xylosyl(coumaroylglucosyl)galactoside (C3x(CG)g).

The term "heterologous DNA sequence" is used in the present application to characterize the sequence of a transgene in a transgenic plant, i.e. as a reference to a DNA sequence incorporated into a plant by a transgenic modification of the plant. The term therefore also encompasses the introduction of a homologous sequence derived from another carrot plant. Transgenic modifications of plants incorporating genes of the same plant species are also identified in the art as cisgenic modifications (described for example in Holme et al., Plant Biotechnology Journal (2012), 10: 237-247).

In particular, the present application encompasses transgenic carrot plants comprising a heterologous DNA sequence of a homolog promoter of a transcription factor gene, i.e. the sequence of a promoter derived from a different carrot plant.

The term "transcription factor" is used in this application to describe a protein that controls the rate of transcription of genetic information from DNA to messenger RNA by binding to a specific DNA sequence. The MYB (myeloblastosis) transcription factor represents a family of proteins that include the conserved MYB DNA-binding domain. MYB proteins can be classified into different subfamilies depending on the number of adjacent repeats in the MYB domain. Plants contain a MYB-protein subfamily, R2R3-MYB, which is characterized by two MYB domain repeats. The basic helix-loop-helix proteins are dimeric transcription factors that are found in almost all eukaryotes. Members of this family have two highly conserved domains that together make up 60 amino acid residues. At the amino-terminal end of this region is the basic domain, which binds the transcription factor to DNA at a consensus hexanucleotide sequence known as the E box. Different families of bHLH proteins recognize different E-box consensus sequences. At the carboxy-terminal end of the region is the HLH domain, which facilitates interactions with other protein subunits to form homo- and hetero-dimeric complexes.

The term "anthocyanins" is used in this application to describe glycosides and acylglycosides of anthocyanidins, which share basic flavan skeleton with other flavonoids (FIG. 2). The basic flavan skeleton, is composed of a 15-carbon phenylpropanoid core (C6-C3-C6), which is arranged into two aromatic rings (A and B) linked by a heterocyclic benzopyran ring (C) (FIG. 1). The C ring of anthocyanidins have two double bonds in cation form, which result in overall positive charge. The anthocyanidin aglycones, i.e. flavylium ion (2-phenylbenzopyrilium) of three most abundant anthocyanins namely pelargonidin (3,5,7,4'-tetrahydroxyflavium), cyanidin (3,5,7,3',4'-pentahydroxyflavylium) and delphinidin (3,5,7,3',4',5'-hexahydroxyflavylium) only differ in their different hydroxyl and methoxyl substitutions (FIG. 2). Structural modifications like glycosylation and acylation or formation of complexes with ions and other phenolic compounds could prevent the degradation of anthocyanins in plants.

The cultivated carrots are broadly divided into two groups, i.e. eastern and western carrots, based on the taproot color. The eastern carrots domesticated in Central Asia, develop purple and yellow taproots, which are often branched. The purple color of the taproot is a result of accumulation of anthocyanin pigments. On the other hand, western carrots appeared in the Netherlands in late 17th to early 18th century are mostly orange, due to accumulation of carotene pigments. References in this application to the terms "black carrot" or "purple carrot" refer to *Daucus carota* ssp. *sativus* var. *atrorubens* Alef., which belongs to the eastern group and develop purple taproots due to accumulation of high percentage of anthocyanins decorated with multiple acylated and methylated sugar moieties. These secondary modifications lead to greater stability and color intensity, which makes them excellent natural dyes to be used for food, cosmetic and pharmaceutical industrial applications. References in this application to the term "orange carrot" refer to carrots that are lack of purple pigmentation and have no detectable amount of anthocyanins.

The term "promoter" is used in this application to describe a region of DNA that initiates transcription of a particular gene. Promoter sequences are typically located directly upstream or at the 5' end of the transcription initiation site. RNA polymerase and the necessary transcription factors bind to the promoter sequence and initiate transcription. References in this application to the term "heterologous promoter" refer to promoters of one species which are able to express a protein in a foreign genus or species, whereas the term "homologous promoter" refers to promoters of one species which are able to express a protein in the same genus or species.

The two transcription factors disclosed in this application, DcMYB90 and DcEGL1, exhibit activity in upregulation of anthocyanin biosynthesis in orange carrots. Expression cassettes and vectors containing these polynucleotide sequences were constructed and introduced into carrot plant cells in accordance with transformation methods and techniques known in the art. Exemplary polynucleotides that are designed for expression in plants and encode the full-length of the DcMYB90 and DcEGL1 proteins are set forth in SEQ ID NO:1 and SEQ ID NO:2. The polynucleotides that are designed for expression in plants may also exhibit at least about 80% to about 100% sequence identity along the length of SEQ ID NO:1 or SEQ ID NO:2, that is 80%, 81%, 82%, 83%, 84%, 85%, 86%, 87%, 88%, 89%, 90%, 91%, 92%, 93%, 94%, 95%, 96%, 97%, 98%, 99%, 100%, or any fraction percentage in this range.

Said transcription factors can be expressed with recombinant DNA constructs in which a polynucleotide molecule encoding the protein is operably linked to genetic expression elements such as a promoter and any other regulatory element necessary for expression in the system for which the construct is intended. Non-limiting example include a plant-functional promoter operably linked to said transcription factor encoding sequences for expression of the protein in plants. A non-limiting example of the plant-functional promoter is the Cauliflower mosaic virus (CaMV) 35S promoter as set forth in SEQ ID NO:3, which is the most frequently used promoter in plant biotechnology. The promoter used for expressing said transcription factors may also exhibit at least about 80% to about 100% sequence identity along the length of SEQ ID NO:3, that is 80%, 81%, 82%, 83%, 84%, 85%, 86%, 87%, 88%, 89%, 90%, 91%, 92%, 93%, 94%, 95%, 96%, 97%, 98%, 99%, 100%, or any fraction percentage in this range.

Transgenic plants, and transgenic plant parts that comprise at least 30% C3x(SG)g in the total anthocyanin concentration are provided herein. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that that comprise at least 30% C3x(SG)g in the total anthocyanin concentration are provided herein. Such plants can be made by introducing a recombinant polynucleotide that encodes any one or more of the DcMYB90-type and DcEGL1-type proteins provided in this application into an orange carrot plant cell, and selecting a plant derived from said plant cell that expresses said proteins. In certain embodiments, said orange carrot plant does not naturally express DcMYB90 and DcEGL1. In other embodiments, the DNA is introduced into the carrot plant by Agrobacterium-mediated transformation known in the art.

EXAMPLES

In view of the foregoing, those of skill in the art should appreciate that changes can be made in the specific aspects which are disclosed and still obtain a like or similar result without departing from the spirit and scope of the invention.

Example 1

Cloning of Coding Sequences of DcMYB90 and DcEGL1 and Construction of Transformation Vector The open reading frames (ORF) of DcMYB90 (MYB90-like; NCBI Gene ID: LOC108221186) and DcEGL1 (EGL1; NCBI Gene ID: LOC108210744) were identified by blasting the corresponding Arabidopsis homologous genes against the reference genome published for orange carrot. The coding sequences were amplified from cDNA synthesized from both inner and outer purple tissues of 'Night Bird' taproots by PCR using Phusion® High-Fidelity DNA Polymerase (NEB, U.K.) with primers listed in FIG. 1. The PCR fragments were purified from the gel and cloned into pCR™-Blunt II-TOPO® vector (ThermoFisher Scientific, CA, USA) following the manufacturer's instructions. Three clones of each gene were sequenced by sanger sequencing using standard M13 primers. The positive clones were named pTOPO-M90 (A-C) and pTOPO-E1 (A-C).

An Agrobacterium transformation vector containing coding sequences of DcMYB90 and DcEGL1 under CaMV 35S promoter was created in 3 steps (FIG. 8). In the first step, individual components of the entry vectors named pE-M90 M1 (for DcMYB90) and pE-E1 M2 (for DcEGL1) were amplified from their respective source plasmids by PCR using Phusion® High-Fidelity DNA Polymerase (NEB, U.K.) with overlapping infusion primers listed in FIG. 2. To obtain individual entry vectors for DcMYB90 and DcEGL1 in the second step, the respective components for both entry vectors were assembled using the In-Fusion® HD Cloning Kit (Takara Bio USA, USA) as described by the manufacturer. The integration of the overexpression cassette was confirmed by PCR and Sanger sequencing. The overexpression cassette of Blue Florescent Protein (BFP) (Addgene 14891) was cloned into the pBRACT102 based destination vector 28 linearized with XhoI and SacI. The individual overexpression cassettes of DcMYB90 and DcEGL1 from respective entry vectors were cloned into the destination vector by Golden Gate cloning using AarI as restriction enzyme in the third step, to obtain the final transformation vector named pTM90-E1. The pTM90-E1 was confirmed by PCR and Sanger sequencing; and transformed into Agrobacterium tumifaciens strain AGL0 30 for Agrobacterium-mediated stable transformation of hypocotyls.

Example 2

Simultaneous DcMYB90 and DcEGL1 Expression Leads to Purple Pigmentation in Orange Carrot The orange carrot cultivar 'Danvers 126' (*Daucus carota* subs. *sativus;* 2n=2x=18) was transformed with pM90-212 EGL1 containing the ORFs of DcMYB90 and DcEGL1 under the control of the CaMV 35S promoter by Agrobacterium-mediated stable transformation. Pink/purple spots started appearing on the transformed calli after 6-10 weeks on selection medium. The pigmented calli were selected and transferred to fresh plates every 4 weeks. After 2-3 rounds of sub-culturing, some of the calli had turned completely purple. Purple calli were transferred to regeneration media for embryo and shoot development. The regenerated plantlets were acclimatized and transferred to the greenhouse where they were grown in 2 L pots with peat. The taproots were harvested 3 months after transfer to the greenhouse, which are referred as 3-month-old taproots. Taproots from six individual transgenic plants were harvested and these showed variable pigmented taproots ranging from almost completely purple to almost completely orange. Two individual plants with almost completely purple taproots were selected for further analysis.

DNA was isolated and transformants were analyzed by PCR for holding the kanamycin selection gene. An additional two sets of primers, previously used for amplification of coding sequences were re-used for PCR analysis: (1) DcMYB90 primers to amplify a 882 bp region of the DcMYB90 CDS and (2) DcEGL1 primers to amplify a 1785 bp region of the DcEGL1 CDS. Primers used for DcMYB90 and DcEGL1 amplification are listed in FIG. 1.

Figure 9:
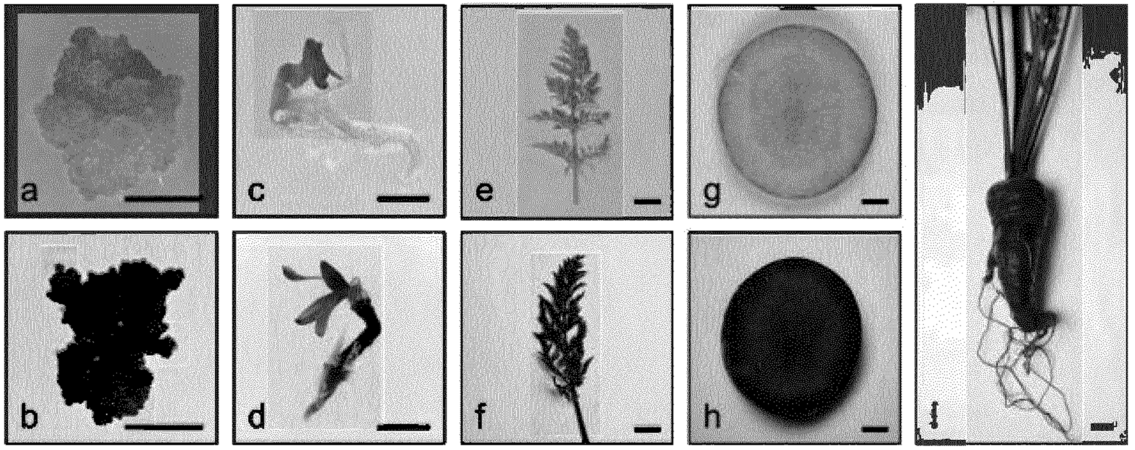
FIG. 9 shows the development of carrots from callus to mature plants.

After transformation, some of the calli developed intense purple pigmentation after 10 to 14 weeks of incubation on selection medium as compared to yellowish/colorless control calli (FIG. 9A, B). The pigmented calli maintained the pigmentation throughout the subsequent sub-culturing. The transformation resulted in six independent transgenic $T_0$ plants, where integration of the coding sequences of the kanamycin selection gene, DcMYB90 and DcEGL1 were confirmed by PCR. Two of the six plantlets, regenerated from deep purple colored calli, led to the formation of deep purple colored plantlets. These two plantlets were selected for further analysis and were named pTM90_E1_L1 and pTM90_E1_L2, abbreviated as L1 and L2, respectively. Plantlets regenerated from light purple calli were less purple and control plantlets were pale-green/colorless (FIG. 4 C, D). The two dark purple plantlets (L1 and L2) maintained the purple pigmentation in leaves, stems and shoots after transfer to peat pots in the greenhouse and stayed purple throughout the development of the plants (FIG. 9 E, F). Wild-type leaves, stems and shoots on the other hand, stayed green throughout development. After three months, the two transgenic plants L1 and L2 had dark green leaves with purple branches as compared to light green leaves and branches of wild-type control plants. The taproots of both L1 and L2 were deeply pigmented as compared to orange taproots of wild-type plants (FIG. 9 G, H, I). The taproots of L1, L2 were selected for thorough analysis.

Example 3

Identification and Characterization of Anthocyanins in the Taproot of Transgenic $T_0$ Plants Expressing DcMYB90 and DcEGL1

Sample Preparation

Approximately 40 g of 3-month-old individual taproots was coarsely grounded (rest stored in −80° C. freezer for RNA extraction); followed by homogenization in a Waring® two-speed commercial blender (VWR-Bie & Berntsen, Herlev, Denmark) in 3% $H_2SO_4$ (1/1, w/w). The homogenate was subsequently mixed with 70% ethanol (1/2, w/w), vortexed and incubated for 1 hour at room temperature. The extract was spun at 4500 rpm for 20 minutes and the supernatant was utilized for further analysis.

Determination of Total Monomeric Anthocyanin Content

The total monomeric anthocyanin content (TMA) in the taproot samples was determined by pH differential method with slight modification. The supernatant was diluted (1:20) with 0.2 M KCL-HCL (pH1) solution and the absorption was recorded between 350 to 700 nm using a UV-visible spectrophotometer (Thermo Scientific Evolution™ 220, Waltham, MA, USA). The resultant TMA was expressed as cyanidin-3-glucoside equivalents in mg g−1.

High Performance Liquid Chromatography-Diode Array Detection (HPLC-DAD)

The individual anthocyanins were determined by comparison of retention time and UV/visible spectroscopic data to previously reported data in black carrots. The relative abundance was calculated by integration of chromatogram peak area generated by HPLC-DAD. The tap-root samples were filtered through a 0.45 μm membrane filter and injected into Elite Lachrom HPLC system coupled with a photodiode array detector (L2450), pump, and au-to sampler (L2200, EZ Chrom Elite software) using a Lichrosorb RP-18 column (5 μm, 4.6 mm×250 m) (Alltech, Copenhagen, Denmark). The elution flow rate was set at 0.8 mL min-1 and the mobile phase was composed of a gradient of (A) water/formic acid/acetonitrile (87/10/3, v/v/v) and (B) water/formic acid/acetonitrile (40/10/50; v/v/v). The data acquisition was performed in the wavelength range from 250 nm to 700 nm during elution gradient of 0 min, 6% B; 20 min, 20% B; 35 min, 40% B; 40 min, 60% B; and 45 min, 90% B, followed by a 10-min equilibration period.

Nano Ultra Pressure Liquid Chromatography Coupled to (Quadrupole) Time-of-Flight Mass Spectrometry (LC-MS/Q-TOF)

A parallel anthocyanin profile were generated by Nano-UPLC coupled by ESI to a Q-TOF Premier (Waters, Milford, USA) MS to confirm the anthocyanins profile obtained by HPLC-DAD. Taproots samples were freeze dried and subsequently pulverized by steel balls using Geno/Grinder® (MiniG, SPEX SamplePrep Inc., NJ, USA). The soluble anthocyanins were extracted from 100 mg of dry taproot powder by shaking in 1 ml of 95% methanol and 5% formic acid for 1 hour at room temperature. The extracted mixture was filtered by 0.22 μm centrifugal filters (Durapore®-PVDF, Merck Millipore, Darmstadt, Germany) and the pass through was diluted opportunely prior to injection to the Acquity Nano-UPLC system (Waters, Milford, USA).

Samples were diluted in 0.1% formic acid (FA) and injected in triplicate runs onto an Xbridge BEH130 C18 5 μm desalting/trap column on-line with a BEH300 C18 1.7 μm Nano-UPLC analytical capillary column (100 μm×100 mm) using an Acquity Nano-UPLC-LC system inter-faced with a Nano ESI source to a Q-TOF Premiere MS (Waters, Milford, MA, USA). The entire length of the LC run was 46 min. The linear gradient was from 0 to 20% Acetonitrile (ACN) in 0.1% FA. Data acquisition was performed by Masslynx software version 4.1 (Waters, Milford, MA, USA) in V positive mode with Glu-Fib-B as calibrant (m/z 785.8426) and lock mass. MS and MS/MS data were recorded in MSe mode (MS1 scan every 1.5 s at 10,000 FWH resolution and MS/MS fragmentation of all ions every 1.5 s) and MS/MS mode (DDA, Data Depending Analysis). MSe acquisitions were run at 5 kV at MS survey (MS1) and 54 kV at MS/MS all ion fragmentation mode. Under these MS/MS condition, all the anthocyanins were fragmented to their respective anthocianidins aglycons. The cyanidin chloride and peonidin chloride (Sigma Aldrich, USA) were used as standards to create dilution series from 0.3 to 10 ng and MSe profiles were acquired using the above-mentioned MS conditions. The exact mass was calculated using the built-in MassLynx MassEnt3 algorithm and corrected for the ppm error for the entire run by the help of the MS/MS calibrant profile (Glu-Fib-B) and the Masslynx tool Accurate Mass Measure. Profile runs were corrected for ppm errors (+/−10 257 ppm) creating centroid runs by the means of Accurate Mass Measure before further quantification by MS-DIAL. Anthocyanins were identified by MS1 survey profile and MS/MS fragmentation using a custom MSP database by MS-DIAL. Quantification has been based on the fragmentation of the anthocyanins by an acquisition with a MS1 survey mode that was using 54 kV as collision energy generating a fragmented aglycon. The MD-DIAL quantification was performed by integration either the MS survey (MS1) and the MS/MS (MSe function 2, MS2) peak areas of the aglycon of the anthocyanins of interest. Final quantification was calculated by quantification of the anthocyanin peak area using a standard curve of the related aglycon ion specie (i.e. cyanidin, or peonidin) and by computing the dilution factor.

Results of HPLC Analysis

HPLC analysis of L1 and L2 revealed accumulation of cyanidin based anthocyanins in purple taproots (FIG. 3). high levels of anthocyanin in L1 and L2 were confirmed by parallel LC-MS/Q-TOF analysis, which also revealed low levels of anthocyanins in L3 to L6. The average total monomeric anthocyanin (TMA) content in L1 and L2 was calculated to be 2.03 and 1.8 mg/g FW respectively, out of which 97.5% of the anthocyanins were mono-acylated (FIG. 4). In comparison, the TMA of the two black carrot cultivars 'Deep Purple' and Night Bird was estimated to be between 1.5 to 2.2 and 2.0 to 2.4 mg/g FW, respectively. A total of 5 anthocyanins, i.e. cyanidin 3-xylosylgalactoside [C3xg], cyanidin 3-xylosyl(glucosyl)galactoside [C3x(G)g], cyanidin 3-xylosyl(coumaroylglucosyl)galactoside [C3x(CG)g], cyanidin 3-xylosyl (feruloylglucosyl)galactoside [C3x(FG)g] and cyanidin 3-xylosyl(synapoylglucosyl)galactoside [C3x(SG)g] were detected by HPLC analysis of the purple taproots of Deep Purple, Night Bird, L1 and L2 (FIG. 4, FIG. 10). Whereas, no anthocyanins were detected in orange taproot of Danvers wild type control plants. Due to different extraction methods between HPLC and LC-MS, C3x(CG)g of transgenics was only found in the HPLC profile. The HPLC profile of the purple taproots of L1 and L2 was confirmed by LC-MS/Q-TOF analysis (FIG. 5). C3x(SG)g, was the most abundant anthocyanin present in the taproots of L1-L6 (FIG. 5). For Night Bird, the most abundant anthocyanin was C3xg. No anthocyanins were detected in the wild type orange carrot cv. Danvers.

Black carrots have a high content of acylated anthocyanins. Acylated anthocyanins are much more stable than non-acylated anthocyanins and a high content of these is therefore of great importance when the purpose is to produce anthocyanins for food color. The major mono-acylated anthocyanins in black carrots are C3x(FG)g, C3x(SG)g and C3x(CG)g. There is, however, great variation in the relative content of these in different black carrot cultivars. In the present and other studies, the major mono-acylated anthocyanins found in Deep Purple was C3x(FG)g. In contrast, C3x(SG)g was the major mono-acylated anthocyanin in the taproots of the transformed carrots. Acyl-transferases present in carrot cell suspension protein extracts has been reported to have a higher affinity for 1-O-feruloylglucose than for 1-O-sinapoylglucose as acyl donor. However, as 1-O-sinapoylglucose accumulated at a much higher level in the cultured carrots cells, 1-O-sinapoylglucose was used as the main acyl donor. Thus the higher level of C3x(SG)g in the transformed carrots could indicate that 1-O-sinapoylglucose was more available as acyl donor for acyltransferase than 1-O-feruloylglucose during taproot development.

The constitutive simultaneous overexpression of DcMYB90 and DcEGL1 resulted in consistent upregulation of anthocyanin biosynthesis in all tissues of transgenic orange carrot plants. The upregulation was strictly correlated with the anthocyanin accumulation and pigment intensity. The TMA of transgenic carrots was comparable to the reference black carrots, whereas the percentage of acylated anthocyanins was higher in transgenic carrots. Furthermore, the most abundant anthocyanin in transgenic carrots was C3x(SP)g, whereas the reference black carrot cultivar mostly accumulated C3xg.

Example 4

Real-Time Quantitative PCR Estimation of Gene Expression Activated by the Expression of DcMYB90 and DcEGL1

The expression of transgenes DcMYB90 and DcEGL1 and their effect in regulating anthocyanin pathway was quantified by RT-qPCR in the taproots of two almost completely purple plants L1 and L2 (FIG. 12). Total RNA was extracted and up-concentrated from 3-month-old taproots of confirmed transgenic plants and 1 μg of total RNA was used for cDNA synthesis using SuperScript™ II Reverse Transcriptase (Invitrogen, USA) following manufacturer's instructions. The primer pairs for DcMYB90 and DcEGL1 were designed using Premier primer 5, (PREMIER Biosoft, USA), and subsequently analyzed for amplification specificity and annealing temperature using endpoint PCR on synthesized cDNA. The primer pairs for major biosynthetic genes in carrots are listed in FIG. 3. The RT-qPCR experiments were performed, wherein the Cycle threshold value (Ct) of the target genes were normalized against Act2 (NCBI: X17525) and the relative expression levels of the genes as compared to the non-transformed control was calculated as $-\Delta\Delta Ct$.

No expression of DcMYB90 was detected in any of the examined tissues of wild type Danvers. DcEGL1 was endogenously expressed in leaves and taproots of wild type plants with a $-\Delta Ct$ value of 6 and 4 respectively, normalized against DcActin2. As compared to non-transformed plants, the relative expression level of DcMYB90 in L1 and L2 was up to 18-fold higher in the purple tissue of transformed plants (FIG. 12). Moreover, the expression of DcEGL1 was upregulated by up to 14 folds in the purple tissue compared to wild type (FIG. 12).

In general, the expression DcMYB90 and DcEGL1 resulted in an increase in the mRNA level of phenylpropanoid pathway genes (GPGs) i.e. PAL3, C4H1 and 4CL1 in transgenic calli and purple taproots as compared to wild type. On the other hand, the mRNA level of GPGs was lower in young purple leaves and unchanged in old green leaves as compared to the non-transgenic wild type leaves (FIG. 12).

The anthocyanin pathway genes, both early and late biosynthetic genes (EBGs and LBGs) were upregulated in all transgenic tissue samples and the upregulation strictly correlated with the pigmentation intensity. The relative expression level of anthocyanin pathway genes was highest in the purple taproots (FIG. 9, 11). On an average, the relative expression levels of F3H1, F3'H1, DFR1, LDOX1 and UCGalT1 was 15 to 25 fold higher in the purple taproots as compared to the non-transgenic orange taproots.

These results demonstrate that DcMYB90 and DcEGL1 from the black carrot (purple) cv. Night Bird together activate the anthocyanin biosynthetic pathway in the orange carrot cv. Danvers 126. As DcEGL1 is already weakly expressed in Danvers where no endogenous expression of DcMYB90 can be detected, the results strongly indicates that the absence of DcMYB90 expression in Danvers is causing inactivation of anthocyanin synthesis, that not even low levels of anthocyanins is synthesized in this cultivar. Moreover, the results strongly suggest that DcMYB90 is one of the key regulator of anthocyanin biosynthesis in black carrots, where it together with the compatible bHLH partner DcEGL1 can activate anthocyanin related biosynthetic genes in orange carrots.

The TMA of transgenic carrots was comparable to the reference black carrots, whereas the percentage of acylated anthocyanins was higher in transgenic carrots. Furthermore, the most abundant anthocyanin in transgenic carrots was C3x(SP)g, whereas the reference black carrot cultivar mostly accumulated C3xg. This may be attributed to a higher expression of the DcUSAGT1 gene, which encodes a UDP-glucose: sinapic acid glucosyltransferase (USAGT), catalyzing synthesis of 1-O-sinapoylglucose by forming ester bond between carboxyl-C of sinapic acid and C1 of glucose. Further investigation involving estimation of expression level of various glucosyltransferases in purple and non-purple carrots is required to estimate effect of DcMYB90 and DcEGL1 on them. Moreover, these results indicates that the expression of various structural genes of anthocyanin pathway involved in secondary modification of anthocyanins can be strictly controlled to produce desired secondary modifications, which may be important for the industrial applications.

In summary, DcMYB90 and DcEGL1 is the first set of carrot transcription factors reported capable of activating anthocyanin biosynthesis in orange taproots and they constitutes important handles for future exploitation of anthocyanin's from the carrot taproot.

Example 5

Cloning of Coding Sequences of AmRosea1 and AmDelila and Construction of Transformation Vector The coding sequence of AmRosea1 (GenBank: DQ275529.1) was amplified by PCR using Phusion® High-Fidelity DNA Polymerase (NEB, U.K.) from pRosea (GB0026; Addgene plasmid #68194) kindly provided by Diego Orzaez Lab, IBMCP, Spain, using the infusion primers listed in FIG. 13. The forward primer was designed with 8 bp overhang complimentary to the CaMV 2×35S promoter and the unique restriction site for NcoI, whereas the reverse primer consisted 9 bp overhang for NOS terminator with the unique restriction site for HindIII for modular editing. The CaMV 2×35S promoter and NOS terminator was amplified from pCambia-1300-35Su plasmid using infusion primer pairs. The primer pair for CaMV 2×35S were designed with the restriction sites for XhoI spanned with destination vector specific 9 bp overhang for forward primer and AmRosea1 specific 10 bp overhang followed by unique restriction site for NcoI in reverse primer respectively (FIG. 13). The primer pair for NOS terminator was designed with the unique restriction sites for HindIII and EcoRI, preceded by AmRosea1 and the destination vector specific overhangs (FIG. 13). All three PCR products with overlapping overhangs were cloned into pGreen/pSoup based pBRACT102 linearized with XhoI and EcoRI, using In-Fusion® HD Cloning Kit (Takara Bio USA, USA) as per manufacturer instructions to obtain transformation vector containing the AmRosea gene. This resulting vector was named pRos1 (FIG. 17*a*). Similarly, the transformation vector containing the AmDelila gene was created by cloning PCR products containing overlapping overhangs of the coding sequence of AmDelila, amplified from the coding sequence of AmDelila (GB0079; Addgene plasmid #68200), the CaMV 2×35S and the NOS terminator using infusion primers (FIG. 13) into pBRACT102, linearized with EcoRI and SacI. This vector is hereafter referred to as pDel (FIG. 17*b*). Finally, the expression cassette of the pDel (2×35S:AmDEL:NOS) transformation vector was amplified with infusion primer pair with overhangs specific to pRos1 (FIG. 13) and cloned into pRos1 linearized with PstI to obtain the transformation vector containing both the AmRosea1 and the AmDelila genes. This resulting vector was named pRD (FIG. 17*c*). The pRos1, pDel and pRD vectors (FIG. 17) were confirmed by sanger sequencing and transformed into Agrobacterium tumifaciens strain AGL0 for Agrobacterium-mediated stable transformation of hypocotyls.

Example 6

Simultaneous AmRosea1 and AmDelila Expression in Transgenic Carrots Via Agrobacterium Mediated Hypocotyl Transformation In total 100, 84 and 121 explants were infected with pRos, pDel and pRD transformation vectors respectively. We obtained 88, 40 and 87 calli from these explants, respectively. The infected explants started developing calli within 3-4 weeks of transfer to Selection Medium II (FIG. 14). For the pRD infected explants, around 30% of the calli developed pink/magenta pigmentation after 6 weeks of culture. These calli were selected and turned into completely purple during subsequent selection and sub-culturing (FIG. 18*b,c*). On the other hand, no pigmentation was visible in any of the calli induced on non-infected explants as well as on calli induced on explants infected with pRos1 or pDel, and they all remained yellowish-white throughout subsequent sub-culturing (FIG. 18*a*). PCR analysis was performed on 11, 8, 9 plantlets regenerated from pRos, pDel and pRD infected explants, respectively. These confirmed the integration of the T-DNA expression cassette. They all showed the amplification of a 679 bp fragment encompassing the nptII and CaMV terminator (FIG. 19). The plantlets regenerated from the pRos1 and the pRD infected explants showed the amplification of a 663 bp region of the AmRosea CDS and the plantlets regenerated from the pDel and the pRD infected explants showed the amplification of a 1935 bp region of the AmDelila CDS (FIG. 19).

The hypocotyls and roots of the pRD transformed plantlets were dark purple (FIG. 18*e*) whereas the hypocotyls and roots of the non-transformed plantlets were white to pale green (FIG. 18*d*). During the further growth in the greenhouse, the stems of the pRD trans-formed plants remained deeply pigmented throughout the following 3 months. The young leaves were also dark purple and matured into dark green leaves during the sub-sequent growth (FIG. 18*g*). In contrast, no such pigmentation was visible in non-transformed plants (FIG. 18*f*). Furthermore, the color of the 3-month-old taproots from the pRD trans-formed plants were purple (FIG. 18*h,i*), compared to the orange color of taproots from the non-transformed plants (FIG. 18*j*). The epidermis, cortex, and sheath cells of taproots from the pRD transformed plants accumulated purple pigments against a slight orange back-ground whereas, the endodermis, pericycle and lateral roots were completely purple (FIG. 18*h*). In contrast, the pRos1 and pDel transformed plants showed the same colors in the stems and leaves as the non-transformed plants throughout their development in the greenhouse, and the 3-monts-old taproots also showed the same orange color as the tap-roots of the non-transformed plants (FIG. 18*k,l*).

Example 7

Relative Expression Levels of Target Genes Activated by Expression of AmRosea1 and AmDelila The expression of the transgenes AmRosea1 and AmDelila and their influence on the anthocyanin pathway was quantified by RT-qPCR in taproots of one pRos1 transformed plant, one pDel transformed plant and six pRD transformed plants. No expression of either AmRosea1 or AmDelila were observed in the non-transformed carrots. Compared to the non-transformed control plants, the expression level of the AmRosea1 gene increased 9.8 fold in the pRos1 transformed plant and 14.45 fold in average in the pRD transformed plants (FIG. 20*a*). Similarly, the AmDelila transcripts increased 5.54 fold in the pDel trans-formed plant and 14.73 fold in average in the pRD transformed plants (FIG. 20*a*).

The expression of AmRosea1 in the pRos1 transformed plant led to upregulation of the general phenylpropanoid pathway genes PAL3, C4H1 and 4CL1. These were upregulated 2.28, 5.80 and 4.41 fold, respectively (FIG. 20*b*). In contrast, the expression of AmDelila in the pDel transformed plant led to a slight upregulation of only C4H1 by 1.86 fold whereas PAL3 was slightly downregulated by 0.51 fold and no expression of 4CL1 was detected (FIG. 20*b*). On the other hand, the simultaneous expression of AmRosea1 and AmDelila in the pRD transformed plants resulted in the upregulation of PAL3, C4H1 and 4CL1 by 4.60, 6.81 and 5.03 fold, respectively (FIG. 20*b*).

The expression of AmRosea1 in the pRos1 transformed plant and the AmDelila in the pDel transformed plants did not result in any upregulation of anthocyanin pathway genes. In contrast, the simultaneous expression of both AmRosea1 and AmDelila in the pRD trans-formed plants led to consistent upregulation of all major genes driving the flux towards anthocyanin biosynthesis (FIG. 20*b*). On an average, CHS1, CHI1, F3H1, F3'H1, DFR1, LDOX1 and UCGalT1 were 15.38, 7.98, 12.94, 14.62, 11.68, 14.46 and 14.07 fold higher in the pRD transformed plants as compared to the non-transformed controls (FIG. 20*b*).

Example 8

Identification and Characterization of Anthocyanins in Taproots of Transgenic Plants Expressing AmRosea1 and AmDelila Anthocyanins detected in the 3-month-old taproots of the pRD-transformed plants using HPLC and LC-MS/Q-TOF were compared to results obtained from the black carrot cultivar Deep Purple used as a black carrot reference in this study. The HPLC analysis of the 3-month-old pRD transformed taproots and Deep Purple taproots identified six cyanidin-based anthocyanins, which have all been previously identified in Deep Purple by Montilla et al. (2011) i.e. cyanidin 3-xylosyl (glucosyl) galactoside [C3x(G)g], cyanidin 3-xylosylgalactoside [C3xg], cyanidin 3-xylosyl (synapoylglucosyl) galactoside [C3x(SG)g], cyanidin 3-xylosyl (feruloylglucosyl) galactoside [C3x(FG)g], cyanidin 3-xylosyl (coumaroylglucosyl) galactoside [C3x(CG)g] and peonidin 3-xylosyl (synapoylglucosyl) galactoside [P3x(SG)g]. The relative abundance of the six anthocyanins was calculated as the percentage peak area from the HPLC chromatograms. The abundance of these anthocyanins were different in the pRD-transformed taproots as compared to the taproots of Deep Purple (FIG. 15). The HPLC analysis showed that the most abundant anthocyanin in the pRD-transformed taproots was C3x(SG)g which accounted for 78 to 88% of the total anthocyanins identified. In contrast, the most abundant anthocyanin in Deep Purple was C3x(FG)g and it accounted for 71% of the total anthocyanins (FIG. 15). The HPLC results were confirmed by the LC-MS/Q-TOF analysis (FIG. 16). Due to different extraction methods between HPLC and LC-MS no C3x(CG)g and only trace amounts of C3xg were detected by LC-MS/MS. Thus, only four of the HPLC identified cyanidin-based anthocyanins were quantified by LC-MS/MS (FIG. 16). Yet, the most abundant cyanidin based anthocyanidin in the pRD transformed tap-roots were still C3x(SG)g accounting for 71 to 98% of the total anthocyanins identified in the LC-MS/MS analysis as compared to 78 to 88% in the HPLC analysis (FIG. 15 and FIG. 16).

The total monomeric anthocyanin content (TMA) in the taproot tissue extracts was calculated to range between 1.24 to 2.45 mg g−1 (FW) among the pRD transformed plants (FIG. 20*c*) as compared to 1.50 to 1.90 mg g−1 (FW) in Deep Purple 32. Only trace amount of monomeric anthocyanins were detected in taproots of non-transformed, pRos1 transformed and pDel transformed plants. Based on the dry weight from LC-MS/MS quantification, the overall content of soluble anthocyanins ranged from 5.82 to 44.38 mg g-1 DW in the pRD transformed taproots as compared to 23.82 mg g−1 DW in Deep Purple (FIG. 16).

The invention claimed is:

1. A transgenic carrot plant comprising:

a. at least one heterologous DNA sequence consisting of the transcription factor gene DcMYB90 (SEQ ID NO:1) operably linked to a heterologous promoter and at least one heterologous DNA sequence consisting of the transcription factor gene DcEGL1 (SEQ ID NO:2) operably linked to a heterologous promoter; or b. at least one heterologous DNA sequence consisting of the transcription factor gene DcMYB90 having at least 95% identity to the sequence of SEQ ID NO: 1, and at least one heterologous DNA sequence consisting of the transcription factor gene DcEGL1, having at least 95% identity to the sequence of SEQ ID NO:2;

wherein the transcription factor gene DcMYB90 (SEQ ID NO. 1) encodes the transcription factor protein of SEQ ID NO. 5, and the transcription factor gene DcEGL1 (SEQ ID NO. 2) encodes the transcription factor protein of SEQ ID NO. 6, and wherein the co-expression of the proteins increases the expression of sinapic acid glucosyltransferase (USAGT) having the sequence of SEQ ID NO: 4.

2. A DNA sequence consisting of:

(a) a first transcription factor gene DcMYB90 (SEQ ID NO:1) operably linked to a heterologous promoter, and a second transcription factor gene DcEGL1 (SEQ ID NO:2) operably linked to a heterologous promoter; or (b) a first transcription factor gene having a sequence with at least 95% identity to the sequence of SEQ ID NO:1 operably lined to a heterologous promoter, and the second transcription factor gene have a sequence with at least 95% identity to the sequence of SEQ ID NO: 2, operably linked to a heterologous promoter;

wherein the first transcription factor gene DcMYB90 (SEQ ID NO. 1) encodes the transcription factor protein of SEQ ID NO. 5, and the transcription factor gene DcEGL1 (SEQ ID NO. 2) encodes the transcription factor protein of SEQ ID NO. 6, and wherein the co-expression of the proteins increases the expression of sinapic acid glucosyltransferase (USAGT) having the sequence of SEQ ID NO:4, and wherein the heterologous promoter achieves an increase in expression of more than 30% in comparison to the expression of the corresponding transcription factor under its natural promoter.

3. The DNA sequence according to claim 2, wherein the heterologous promoter is:

(a) the CaMV 35 S promoter comprising the sequence of SEQ ID NO:3; or (b) a sequence having at least 99% identity to the sequence of SEQ ID NO: 3, which sequence achieves an expression of a coding sequence in a plant cell of at least 99% of the sequence of SEQ ID NO:3.

4. A method of producing a carrot plant comprising transforming an orange carrot plant with:

a. (a) at least one DNA sequence consisting of the transcription factor gene DcMYB90 (SEQ ID NO:1) operably linked to a heterologous promoter and at least one heterologous DNA sequence consisting of the transcription factor gene DcEGL1 (SEQ ID NO:2) operably linked to a heterologous promoter; of b. at least one DNA sequence having at least 95% identity to the sequence of SEQ ID NO:1, and at least one DNA sequence having at least 95% identity to the sequence of SEQ ID NO:2 operably linked to a heterologous promoter;

wherein the transcription factor gene DcMYB90 (SEQ ID NO:1) encodes the transcription factor protein of SEQ ID NO; 5, and the transcription factor gene DcEGL1

(SEQ ID NO:2) encodes the transcription factor protein of SEQ ID NO: 6, and wherein the co-expression of the proteins wherein the heterologous DNA sequence increases the expression of sinapic acid glucosyltransferase (USAGT) having the sequence of SEQ ID NO:4.

5. The method of claim 4, wherein the heterologous promoter is:

(a) the CaMV 35 S promoter comprising the sequence of SEQ ID NO:3 or (b) a sequence having at least 99% identity to the sequence of SEQ ID NO: 3, wherein the sequence achieves an expression of a coding sequence in a plant cell of at least 99% of the sequence of SEQ ID NO: 3.

6. A method of preparing a composition comprising anthocyanins, the method comprising:

(a) the method of producing a carrot plant according to claim 4; and (b) isolating the composition comprising anthocyanins from the taproot of the carrot plants, wherein the composition comprises cyanidin 3-xylosyl (sinapoylglucosyl)galactoside in a concentration of at least 30% of the total anthocyanin concentration.

7. The carrot plant according to claim 1, wherein the transgenic carrot plant is not *Daucus carota* subsp *sativus* var *atrorubens.*

* * * * *